US010111698B2

(12) United States Patent
Scheib et al.

(10) Patent No.: US 10,111,698 B2
(45) Date of Patent: Oct. 30, 2018

(54) SURGICAL INSTRUMENT WITH ROTATABLE SHAFT HAVING PLURALITY OF LOCKING POSITIONS

(71) Applicant: Ethicon Endo-Surgery, LLC, Guaynabo, PR (US)

(72) Inventors: Charles J. Scheib, Loveland, OH (US); Benjamin D. Dickerson, Cincinnati, OH (US); Matthew C. Miller, Cincinnati, OH (US); Geoffrey S. Strobl, Williamsburg, OH (US); Jeffrey S. Swayze, Hamilton, OH (US); David T. Martin, Milford, OH (US); Daniel J. Mumaw, Liberty Township, OH (US)

(73) Assignee: Ethicon LLC, Guaynabo, PR (US)

( * ) Notice: Subject to any disclaimer, the term of this patent is extended or adjusted under 35 U.S.C. 154(b) by 524 days.

(21) Appl. No.: 14/688,405

(22) Filed: Apr. 16, 2015

(65) Prior Publication Data

US 2016/0302840 A1    Oct. 20, 2016

(51) Int. Cl.
*A61B 17/28* (2006.01)
*A61B 18/00* (2006.01)
(Continued)

(52) U.S. Cl.
CPC ...... *A61B 18/00* (2013.01); *A61B 17/320068* (2013.01); *A61B 17/320092* (2013.01);
(Continued)

(58) Field of Classification Search
CPC ............ A61B 18/00; A61B 17/320068; A61B 17/320092; A61B 2017/2929; A61B 2017/2946; A61B 2017/0019
(Continued)

(56) References Cited

U.S. PATENT DOCUMENTS 5,322,055 A    6/1994  Davison et al.
5,836,960 A   11/1998  Kolesa et al.
(Continued)

FOREIGN PATENT DOCUMENTS

EP    2100562    9/2009

OTHER PUBLICATIONS

U.S. Appl. No. 14/258,179, filed Apr. 22, 2014.
(Continued)

*Primary Examiner* — Michael Carey
(74) *Attorney, Agent, or Firm* — Frost Brown Todd LLC

(57) ABSTRACT

An apparatus comprises a body assembly, a shaft, an end effector, a rotation input feature, and a locking feature. The shaft extends distally from the body assembly and defines a longitudinal axis. The end effector is positioned at the distal end of the shaft. The rotation input feature comprises a proximal end and a distal end. The rotation input feature is configured to rotate one or both of the shaft assembly or the end effector about the longitudinal axis. The locking feature is configured to transition between a locked state and an unlocked state. The locking feature is configured to prevent rotation of the one or both of the shaft assembly when the locking feature is in the locked state. The locking feature is configured to permit rotation of the one or both of the shaft assembly when the locking feature is in the unlocked state.

20 Claims, 18 Drawing Sheets

(51) Int. Cl.
*A61B 17/32* (2006.01)
*A61B 17/29* (2006.01)

(52) U.S. Cl.
CPC ............ *A61B 2017/2929* (2013.01); *A61B 2017/2946* (2013.01); *A61B 2018/0019* (2013.01)

(58) Field of Classification Search
USPC .................................. 606/13, 41, 45, 46, 49
See application file for complete search history.

(56) References Cited

U.S. PATENT DOCUMENTS

| | | | |
|---|---|---|---|
| 5,873,873 A | 2/1999 | Smith et al. |
| 5,897,523 A | 4/1999 | Wright et al. |
| 5,980,510 A | 11/1999 | Tsonton et al. |
| 5,989,264 A | 11/1999 | Wright |
| 6,063,098 A | 5/2000 | Houser et al. |
| 6,090,120 A | 7/2000 | Wright et al. |
| 6,325,811 B1 | 12/2001 | Messerly |
| 6,454,782 B1 | 9/2002 | Schwemberger |
| 6,500,176 B1 | 12/2002 | Truckai et al. |
| 6,589,200 B1 | 7/2003 | Schwemberger et al. |
| 6,752,815 B2 | 6/2004 | Beaupre |
| 6,773,444 B2 | 8/2004 | Messerly |
| 6,783,524 B2 | 8/2004 | Anderson et al. |
| 7,112,201 B2 | 9/2006 | Truckai et al. |
| 7,125,409 B2 | 10/2006 | Truckai et al. |
| 7,135,030 B2 | 11/2006 | Schwemberger et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,621,930 B2 | 11/2009 | Houser |
| 8,461,744 B2 | 6/2013 | Wiener et al. |
| 8,477,595 B2 | 7/2013 | Shousterman et al. |
| 8,591,536 B2 | 11/2013 | Robertson |
| 8,623,027 B2 | 1/2014 | Price et al. |
| 8,888,809 B2 | 11/2014 | Davison et al. |
| 8,939,974 B2 | 1/2015 | Boudreaux et al. |
| 8,986,302 B2 | 3/2015 | Aldridge et al. |
| 9,023,071 B2 | 5/2015 | Miller et al. |
| 9,089,327 B2 | 7/2015 | Worrell et al. |
| 9,095,367 B2 | 8/2015 | Olson et al. |
| 9,161,803 B2 | 10/2015 | Yates et al. |
| 9,204,876 B2 | 12/2015 | Cappola et al. |
| 9,220,559 B2 | 12/2015 | Worrell et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2007/0287993 A1* | 12/2007 | Hinman ............... A61B 17/062 606/1 |
| 2008/0200940 A1 | 8/2008 | Eichmann et al. |
| 2011/0132962 A1* | 6/2011 | Hall ................. A61B 17/07207 227/176.1 |
| 2012/0078243 A1 | 3/2012 | Worrell et al. |
| 2012/0078247 A1 | 3/2012 | Worrell et al. |
| 2012/0112687 A1 | 5/2012 | Houser et al. |
| 2012/0116265 A1 | 5/2012 | Houser et al. |
| 2013/0023868 A1 | 1/2013 | Worrell et al. |
| 2014/0005701 A1 | 1/2014 | Olson et al. |
| 2014/0005703 A1 | 1/2014 | Stulen et al. |
| 2015/0080924 A1 | 3/2015 | Stulen et al. |

OTHER PUBLICATIONS

U.S. Appl. No. 61/410,603, filed Nov. 5, 2010.
International Search Report and Written Opinion dated Oct. 31, 2016 re Application No. PCT/US16/27666.

\* cited by examiner

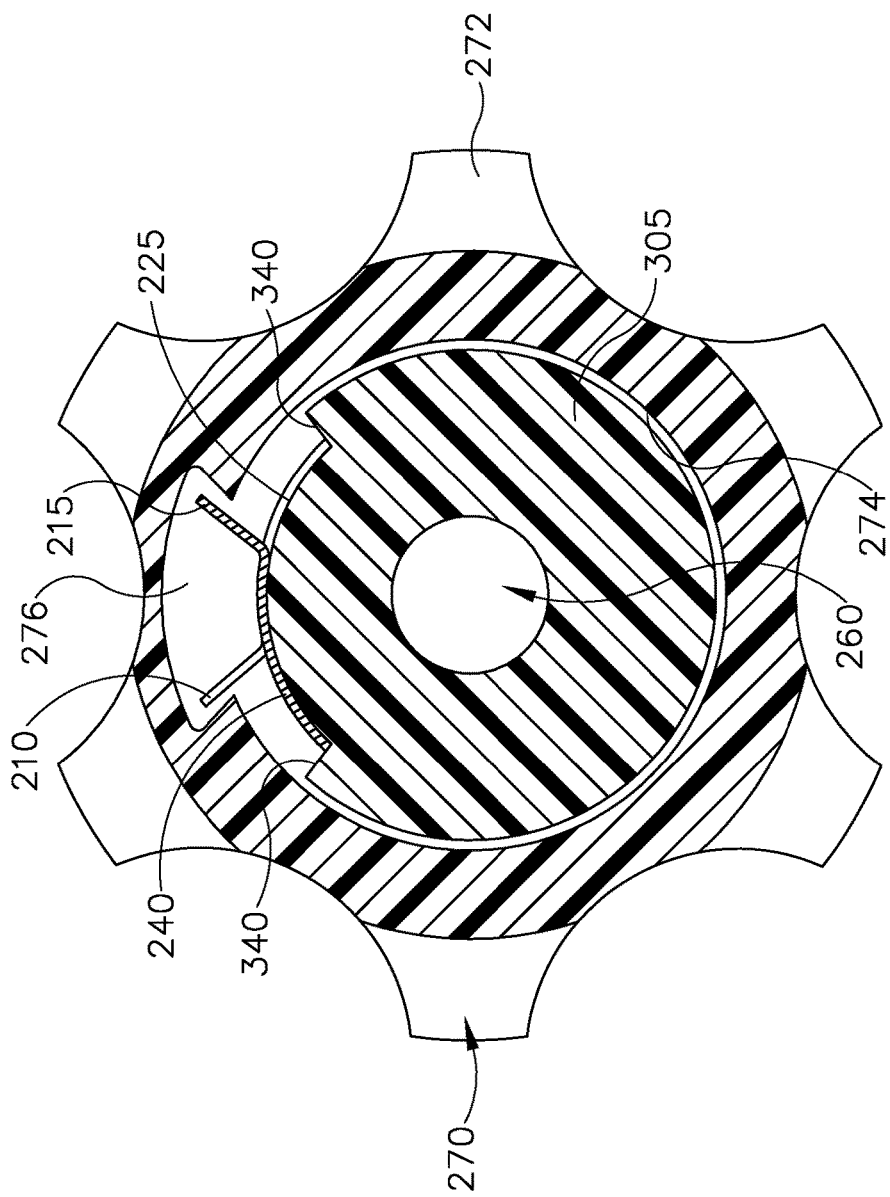

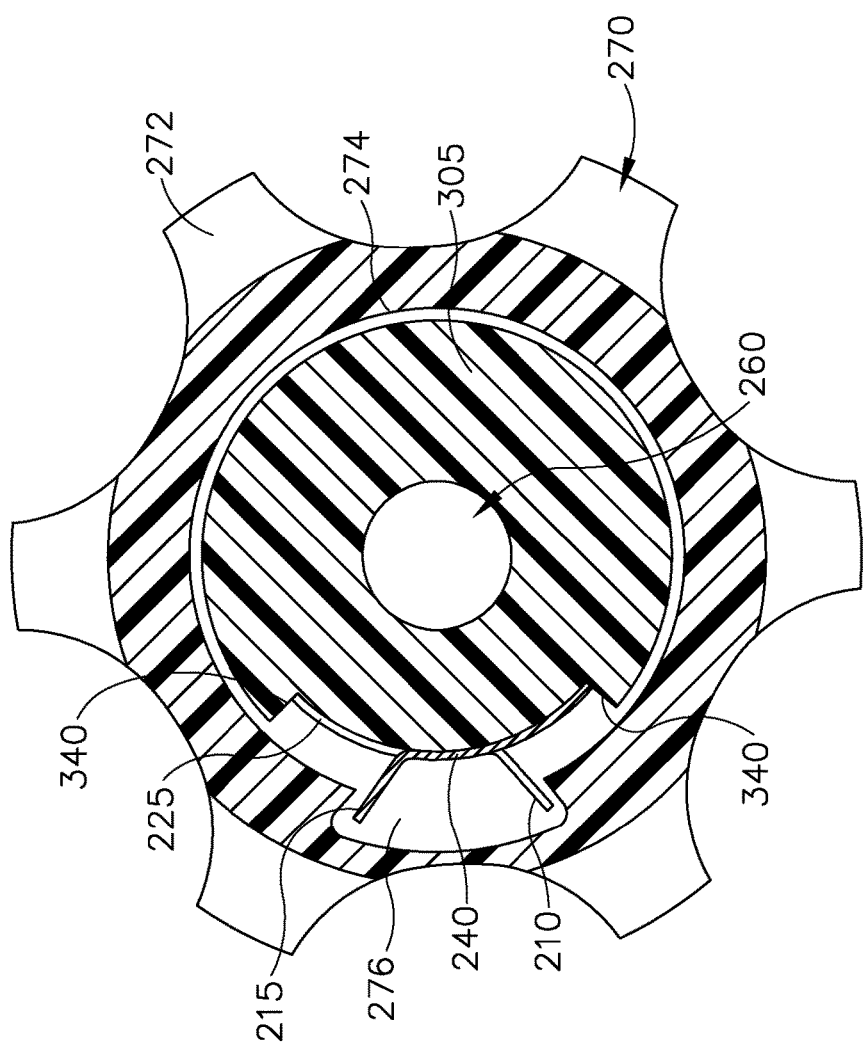

SURGICAL INSTRUMENT WITH ROTATABLE SHAFT HAVING PLURALITY OF LOCKING POSITIONS

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008 now abandoned, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012 now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, entitled "Surgical Instruments with Articulating Shafts," issued as U.S. Pat. No. 9,393,037 on Jul. 19, 2016, the disclosure of which is incorporated by reference herein; U.S. Pub. No. 2014/0005703, entitled "Surgical Instruments with Articulating Shafts," published Jan. 2, 2014, issued as U.S. Pat. No. 9,408,622 on Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein; U.S. Pub. No. 2015/0080924, entitled "Articulation Features for Ultrasonic Surgical Instrument," published Mar. 19, 2015, the disclosure of which is incorporated by reference herein; and U.S. provisional patent application Ser. No. 62/176,880, entitled Ultrasonic Surgical Device with Articulating End Effector," filed Apr. 22, 2014, the disclosure of which is incorporated by reference herein.

A variety of other surgical instruments include a tissue cutting element and one or more elements that transmit radio frequency (RF) energy to tissue (e.g., to coagulate or seal the tissue). An example of such an electrosurgical instrument is the ENSEAL® Tissue Sealing Device by Ethicon Endo- Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; U.S. Pat. No. 8,888,809, entitled "Surgical Instrument with Jaw Member," published Nov. 18, 2014, the disclosure of which is incorporated by reference herein; U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein; U.S. Pub. No. 2012/0078243, entitled "Control Features for Articulating Surgical Device," published Mar. 29, 2012, now U.S. Pat. No. 9,877,720, issued Jan. 30, 2018, the disclosure of which is incorporated by reference herein; U.S. Pub. No. 2012/0078247, entitled "Articulation Joint Features for Articulating Surgical Device," published Mar. 29, 2012, issued as U.S. Pat. No. 9,402,682 on Aug. 2, 2016, the disclosure of which is incorporated by reference herein; U.S. Pub. No. 2013/0030428, entitled "Surgical Instrument with Multi-Phase Trigger Bias," published Jan. 31, 2013, issued as U.S. Pat. No. 9,089,327 on Jul. 28, 2015, the disclosure of which is incorporated by reference herein; and U.S. Pub. No. 2013/0023868, entitled "Surgical Instrument with Contained Dual Helix Actuator Assembly," published Jan. 24, 2013, issued as U.S. Pat. No. 9,545,253 on Jan. 17, 2017, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6A depicts a cross sectional front view of the assembled rotation lock feature of FIG. 3 in a first unengaged position;

FIG. 6E depicts a cross sectional front view of the assembled rotation lock feature of FIG. 3 in the first unengaged position but rotated 90 degrees;

Figure 1:
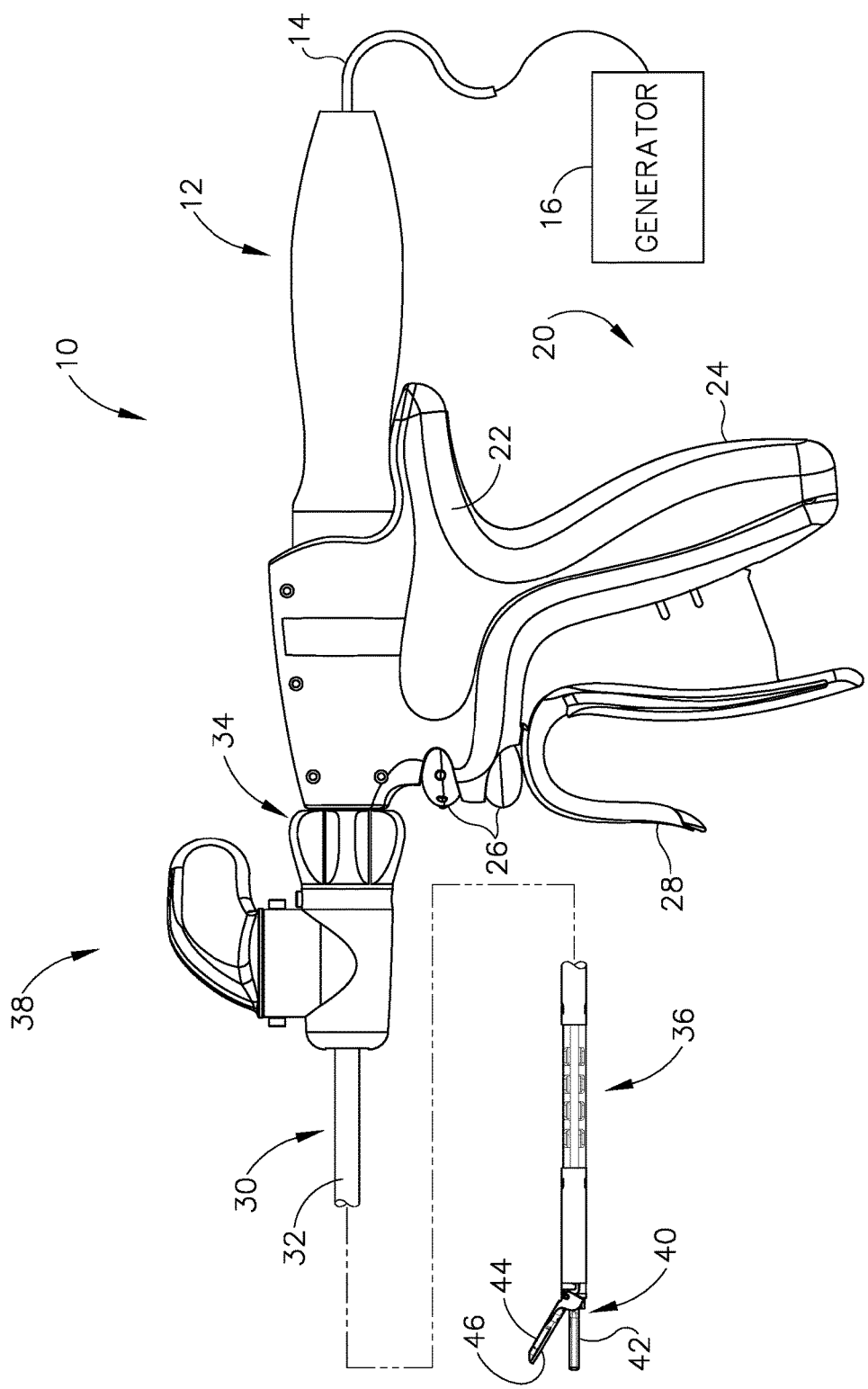
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers to the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (42) and a pivoting clamp arm (44).

Clamp arm (44) is coupled with trigger (28) such that clamp arm (44) is pivotable toward ultrasonic blade (42) in response to pivoting of trigger (28) toward pistol grip (24); and such that clamp arm (44) is pivotable away from ultrasonic blade (42) in response to pivoting of trigger (28) away from pistol grip (24). Clamp arm (44) may thus selectively clamp tissue against ultrasonic blade (42). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1. Clamp arm (44) includes a clamp pad (46) that is secured to the underside of clamp arm (44), facing blade (42). Clamp pad (46) may comprise polytetrafluoroethylene (PTFE) and/or any other suitable material(s). Clamp pad (46) and/or other feature associated with clamp arm (44) may be constructed and operable in accordance with the teachings of any of the various references cited herein.

An ultrasonic transducer assembly (12) extends proximally from body (22) of handle assembly (20). Transducer assembly (12) is coupled with a generator (16) via a cable (14), such that transducer assembly (12) receives electrical power from generator (16). Piezoelectric elements in transducer assembly (12) convert that electrical power into ultrasonic vibrations. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

Blade (42) of the present example is operable to vibrate at ultrasonic frequencies in order to effectively cut through and seal tissue, particularly when the tissue is being compressed between clamp pad (46) and blade (42). Blade (42) is positioned at the distal end of an acoustic drivetrain. This acoustic drivetrain includes transducer assembly (12) and an acoustic waveguide (not shown), which extends through shaft assembly (30) to blade (42). Transducer assembly (12) includes a set of piezoelectric discs (not shown) located proximal to a horn (not shown) of the waveguide. The piezoelectric discs are operable to convert electrical power into ultrasonic vibrations, which are then transmitted along the waveguide (180) to blade (42) in accordance with known configurations and techniques. By way of example only, this portion of the acoustic drivetrain may be configured in accordance with various teachings of various references that are cited herein.

In the present example, the distal end of blade (42) is located at a position corresponding to an anti-node associated with resonant ultrasonic vibrations communicated through the waveguide, in order to tune the acoustic assembly to a preferred resonant frequency $f_o$ when the acoustic assembly is not loaded by tissue. When transducer assembly (12) is energized, the distal end of blade (42) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through the waveguide to reach blade (42), thereby providing oscillation of blade (42) at the resonant ultrasonic frequency. Thus, when tissue is secured between blade (42) and clamp pad (46) of clamp arm (44), the ultrasonic oscillation of blade (42) may simultaneously sever the tissue and denature the proteins in adjacent tissue cells, thereby providing a coagulative effect with relatively little thermal spread. In some versions, an electrical current may also be provided through blade (42) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

Shaft assembly (30) of the present example extends distally from handle assembly (20). Shaft assembly (30) includes an outer sheath (32) that encloses clamp arm (44) drive features and the above-described acoustic transmission features.

Shaft assembly (30) further includes an articulation section (36), which is located at a distal portion of shaft assembly (30), with end effector (40) being located distal to articulation section (36). Articulation section (36) is operable to selectively position end effector (40) at various lateral deflection angles relative to a longitudinal axis defined by outer sheath (32). By way of example only, articulation section (36) may be configured in accordance with one or more teachings of U.S. Pub. No. 2012/0078247, now U.S. Pat. No. 9,402,682, the disclosure of which is incorporated by reference herein. As another merely illustrative example, articulation section (36) may be configured in accordance with one or more teachings of U.S. Pub. No. 2014/0005701, now U.S. Pat. No. 9,393,037 and/or U.S. Pub. No. 2014/0114334, now U.S. Pat. No. 9,095,367, the disclosures of which are incorporated by reference herein. As yet another merely illustrative example, articulation section (36) may be configured in accordance with one or more teachings of U.S. Pub. No. 2012/0078248, entitled "Articulation Joint Features for Articulating Surgical Device," published Mar. 29, 2012, issued as U.S. Pat. No. 9,220,559 on Dec. 29, 2015, the disclosure of which is incorporated by reference herein. Various other suitable forms that articulation section (36) may take will be apparent to those of ordinary skill in the art in view of the teachings herein. In the present example, articulation section (36) is actuated via an articulation control assembly (38), which is located at a proximal end of shaft assembly (30). It should be understood that articulation section (36) is merely optional. As noted further below, articulation section (36) and articulation control assembly (38) may be omitted if desired.

As shown in FIG. 1, a knob (34) is secured to a proximal portion of outer sheath (32). Knob (34) is rotatable relative to body (22), such that shaft assembly (30) is rotatable about the longitudinal axis defined by outer sheath (32), relative to handle assembly (20). Such rotation may provide rotation of end effector (40), articulation section (36), and shaft assembly (30) unitarily. It may be desirable to actuate knob (34) to rotate end effector (40), articulation section (36), and shaft assembly (30) in order to suitably orient the clamping plane of clamp arm (44) and blade (42) relative to targeted tissue.

II. Exemplary Electrosurgical Instrument

Figure 2:
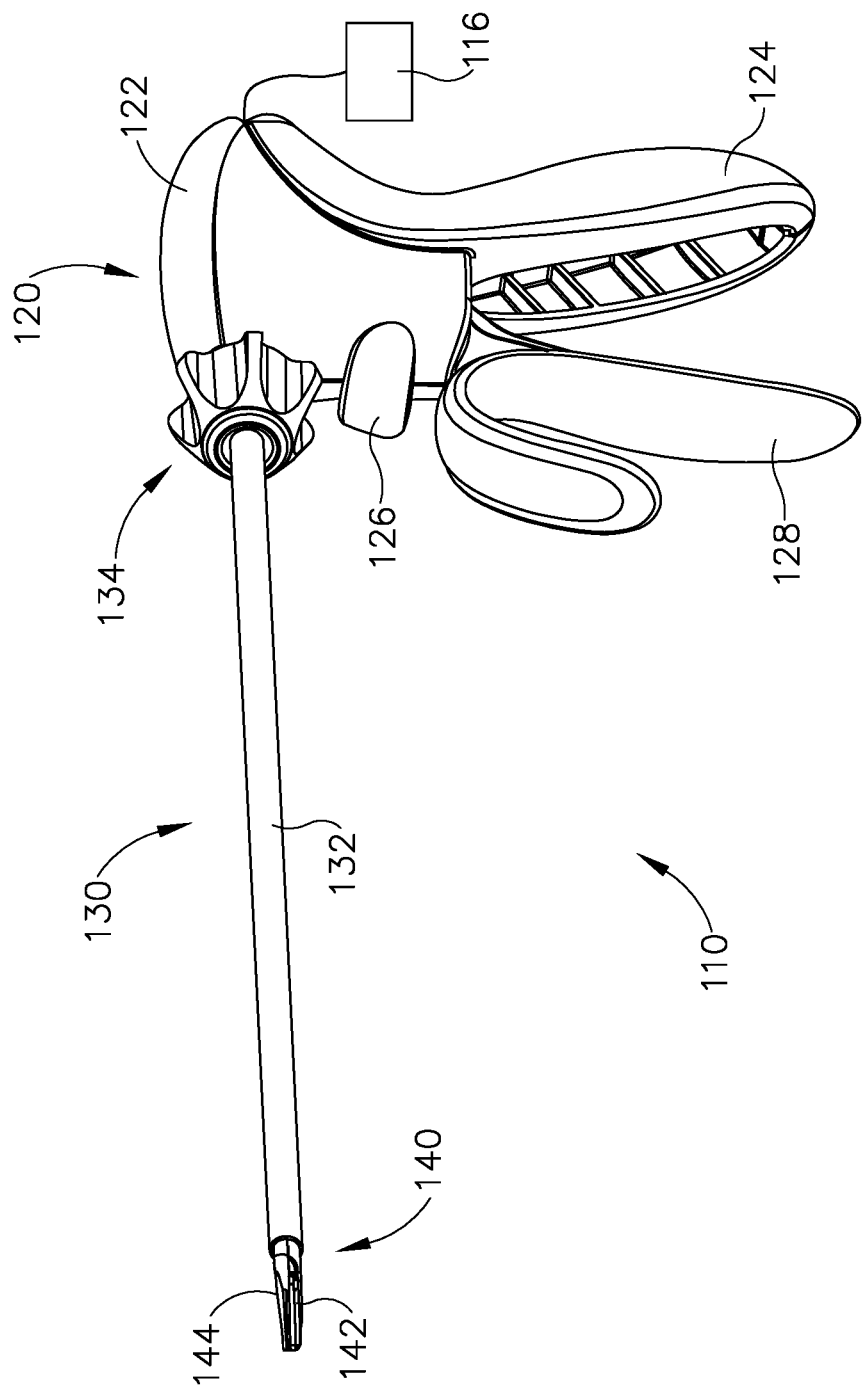
FIG. 2 depicts a side elevational view of an exemplary electrosurgical instrument.

FIG. 2 shows an exemplary electrosurgical instrument (110). By way of example only, electrosurgical instrument (110) may be constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pat. No. 8,888,809; U.S. Pub. No. 2011/0087218, now U.S. Pat. No. 8,939,974; U.S. Pub. No. 2012/0116379, now U.S. Pat. No. 9,161,803; U.S. Pub. No. 2012/0078243, now U.S. Pat. No. 9,877,720, issued Jan. 30, 2018; U.S. Pub. No. 2012/0078247, now U.S. Pat. No. 9,402,682; U.S. Pub. No. 2013/0030428, now U.S. Pat. No. 9,089,327; and/or U.S. Pub. No. 2013/0023868, now U.S. Pat. No. 9,545,253. As described therein and as will be described in greater detail below, electrosurgical instrument (110) is operable to cut tissue and seal or weld tissue (e.g., a blood vessel, etc.) substantially simultaneously. In other words, electrosurgical instrument (110) operates similar to an endocutter type of stapler, except that electrosurgical instrument (110) provides tissue welding through application of bipolar RF energy instead of providing lines of staples to join tissue.

It should also be understood that electrosurgical instrument (110) may have various structural and functional similarities with the ENSEAL®. Tissue Sealing Device by Ethicon Endo-Surgery, Inc., of Cincinnati, Ohio. Furthermore, electrosurgical instrument (110) may have various structural and functional similarities with the devices taught in any of the other references that are cited and incorporated by reference herein. To the extent that there is some degree of overlap between the teachings of the references cited herein, the ENSEAL®. Tissue Sealing Device by Ethicon Endo-Surgery, Inc., of Cincinnati, Ohio, and the following teachings relating to electrosurgical instrument (110), there is no intent for any of the description herein to be presumed as admitted prior art. Several teachings below will in fact go beyond the scope of the teachings of the references cited herein and the ENSEAL®. Tissue Sealing Device by Ethicon Endo-Surgery, Inc., of Cincinnati, Ohio.

Electrosurgical instrument (110) of the present example includes a handle assembly (120), a shaft assembly (130) extending distally from handle assembly (120), and an end effector (140) disposed at a distal end of shaft assembly (130). Handle assembly (120) of the present example includes a body (122), a pistol grip (124), an activation button (126), and a pivoting trigger (128). Trigger (128) is pivotable toward and away from pistol grip (124) to selectively actuate end effector (140) as will be described in greater detail below. Activation button (126) is operable to selectively activate RF circuitry that is in communication with end effector (140), as will also be described in greater detail below. In some versions, activation button (126) also serves as a mechanical lockout against trigger (128), such that trigger (128) cannot be fully actuated unless button (126) is being pressed simultaneously. Examples of how such a lockout may be provided are disclosed in one or more of the references cited herein. It should be understood that pistol grip (124), trigger (128), and button (126) may be modified, substituted, supplemented, etc. in any suitable way, and that the descriptions of such components herein are merely illustrative.

Shaft assembly (130) of the present example includes an outer sheath (132). In some merely illustrative variations, shaft assembly (130) also includes an articulation section (not shown) that is operable to selectively position end effector (140) at various angles relative to the longitudinal axis defined by sheath (132). Handle assembly (120) may include one or more control features that are operable to drive articulation of the articulation section. By way of example only, an articulation section and associated control features may be configured in accordance with at least some of the teachings of the various references cited herein. Of course, as in the present example, shaft assembly (130) may simply lack an articulation section if desired.

End effector (140) of the present example comprises a first jaw (142) and a second jaw (144). In the present example, first jaw (142) is substantially fixed relative to shaft assembly (130); while second jaw (144) pivots relative to shaft assembly (130), toward and away from second jaw (142). In some versions, actuators such as rods or cables, etc., may extend through sheath (132) and be joined with second jaw (144) at a pivotal coupling (not shown), such that longitudinal movement of the actuator rods/cables/etc. through shaft assembly (130) provides pivoting of second jaw (144) relative to shaft assembly (130) and relative to first jaw (142) in response to pivoting of trigger (128) relative to pistol grip (124). Of course, jaws (142, 144) may instead have any other suitable kind of movement and may be actuated in any other suitable fashion.

In the present example, each jaw (142, 144) includes at least one electrode surface that is in communication with an electrical source (116). Electrical source (116) is operable to deliver RF energy to those electrodes at respective polarities such that RF current flows between the electrode surfaces of jaws (142, 144) and thereby through tissue captured between jaws (142, 144). The RF energy may be delivered in response to the operator pressing button (126) while tissue is clamped between jaws (142, 144). While electrical source (116) is shown as being external to electrosurgical instrument (110), electrical source (116) may be integral with electrosurgical instrument (110) (e.g., in handle assembly (120), etc.), as described in one or more references cited herein or otherwise. A controller (not shown) regulates delivery of power from electrical source (116) to the electrode surfaces. The controller may also be external to electrosurgical instrument (110) or may be integral with electrosurgical instrument (110) (e.g., in handle assembly (120), etc.), as described in one or more references cited herein or otherwise. It should also be understood that the electrode surfaces may be provided in a variety of alternative locations, configurations, and relationships.

In some versions, end effector (140) includes one or more sensors (not shown) that are configured to sense a variety of parameters at end effector (140), including but not limited to temperature of adjacent tissue, electrical resistance or impedance of adjacent tissue, voltage across adjacent tissue, forces exerted on jaws (142, 144) by adjacent tissue, etc. By way of example only, end effector (140) may include one or more positive temperature coefficient (PTC) thermistor bodies (e.g., PTC polymer, etc.), located adjacent to the electrodes and/or elsewhere. Data from sensors may be communicated to the controller. The controller may process such data in a variety of ways. By way of example only, the controller may modulate or otherwise change the RF energy being delivered to the electrode surfaces, based at least in part on data acquired from one or more sensors at end effector (140). In addition or in the alternative, the controller may alert the operator to one or more conditions via an audio and/or visual feedback device (e.g., speaker, lights, display screen, etc.), based at least in part on data acquired from one or more sensors at end effector (140). It should also be understood that some kinds of sensors need not necessarily be in communication with the controller, and may simply provide a purely localized effect at end effector (140). For instance, PTC thermistor bodies at end effector (140) may automatically reduce the energy delivery at the electrode surfaces as the temperature of the tissue and/or end effector (140) increases, thereby reducing the likelihood of overheating, in accordance with the teachings of one or more references cited herein. Various ways in which sensors that may be incorporated into electrosurgical instrument (110) will be apparent to those of ordinary skill in the art in view of the teachings herein.

By way of example only, and as is described in various references cited herein, jaws (142, 144) may be actuated and thus closed by longitudinal translation of a firing beam (not shown). The firing beam may be longitudinally movable along part of the length of end effector (140). The firing beam may be coaxially positioned within shaft assembly (130), extend along the length of shaft assembly (130), and translate longitudinally within shaft assembly (130). The firing beam may include a sharp distal blade that severs tissue that is captured between jaws (142, 144). The firing beam may also include a set of flanges that engage jaws (142, 144) and thereby drive jaw (144) toward jaw (142) as the firing beam is advanced distally through end effector (140). The flanges may also drive jaw (144) away from jaw (142) as the firing beam is retracted to a proximal position. The flanges may provide the firing beam with an "I-beam" type of cross section at the distal end of the firing beam. Alternatively, pins or other structural features may be used instead of flanges. In some versions, the firing beam is also electrically grounded, providing a return path for RF energy that is delivered to the captured tissue via the electrodes in jaws (142, 144).

As shown in FIG. 2, a knob (134) is secured to a proximal portion of outer sheath (132). Knob (134) is rotatable relative to body (122), such that shaft assembly (130) is rotatable about the longitudinal axis defined by outer sheath (132), relative to handle assembly (120). Such rotation may provide rotation of end effector (140) and shaft assembly (130) unitarily. It may be desirable to actuate knob (134) to rotate end effector (140) and shaft assembly (130) in order to suitably orient the clamping plane of jaws (142, 144) relative to targeted tissue.

III. Exemplary Shaft Rotation Locking Features

In some instances, it may be desirable to selectively prevent and permit rotatability of shaft assembly (30, 130) relative to handle assembly (20, 120) by locking and unlocking features of shaft assembly (30, 130) relative to handle assembly (20, 120). For instance, it may be desirable to prevent shaft assembly (30, 130) from being inadvertently rotated about its longitudinal axis due to incidental contact between the operator's hand and knob (34, 134), due to incidental contact between end effector (40, 140) and an anatomical structure in the patient, and/or due to other conditions. It may be particularly desirable to prevent shaft assembly (30, 130) from being inadvertently rotated about its longitudinal axis once end effector (40, 140) has been positioned adjacent to targeted tissue, right before or during actuation of clamp arm (44) or second jaw (144) to compress the tissue against blade (42) or first jaw (142), respectively. In the context of instrument (10) where shaft assembly (30) includes an articulation section (36), it may be desirable to prevent rotation of shaft assembly (30) about the longitudinal axis after articulation section (36) has been bent or otherwise deflected to an articulated state. In any of the foregoing scenarios, inadvertent rotation of shaft assembly (30, 130) may frustrate the operator and require the operator to reposition end effector (40, 140) relative to the targeted tissue.

Thus, it may be desirable to provide rotatability of shaft assembly (30, 130) before and during positioning of end effector (40, 140); yet prevent rotatability of shaft assembly (30, 130) once end effector (40, 140) has been suitably positioned relative to targeted tissue. Various examples of how rotatability of shaft assembly (30, 130) may be selectively locked and unlocked will be described in greater detail below. Other examples will be apparent to those of ordinary skill in the art in view of the teachings herein.

While several of the teachings below are described as variations to ultrasonic surgical instrument (10) and/or electrosurgical instrument (110), it should be understood that various teachings below may also be incorporated into various other types of devices. By way of example only, in addition to being readily incorporated into ultrasonic surgical instrument (10) and electrosurgical instrument (110), various teachings below may be readily incorporated into the devices taught in any of the references cited herein, other types of electrosurgical devices, surgical staplers, surgical clip appliers, and tissue graspers, among various other devices. Other suitable devices into which the following teachings may be incorporated will be apparent to those of ordinary skill in the art in view of the teachings herein.

A. Exemplary Knob-Driven Clamping Lock for Shaft Assembly

Figure 3:
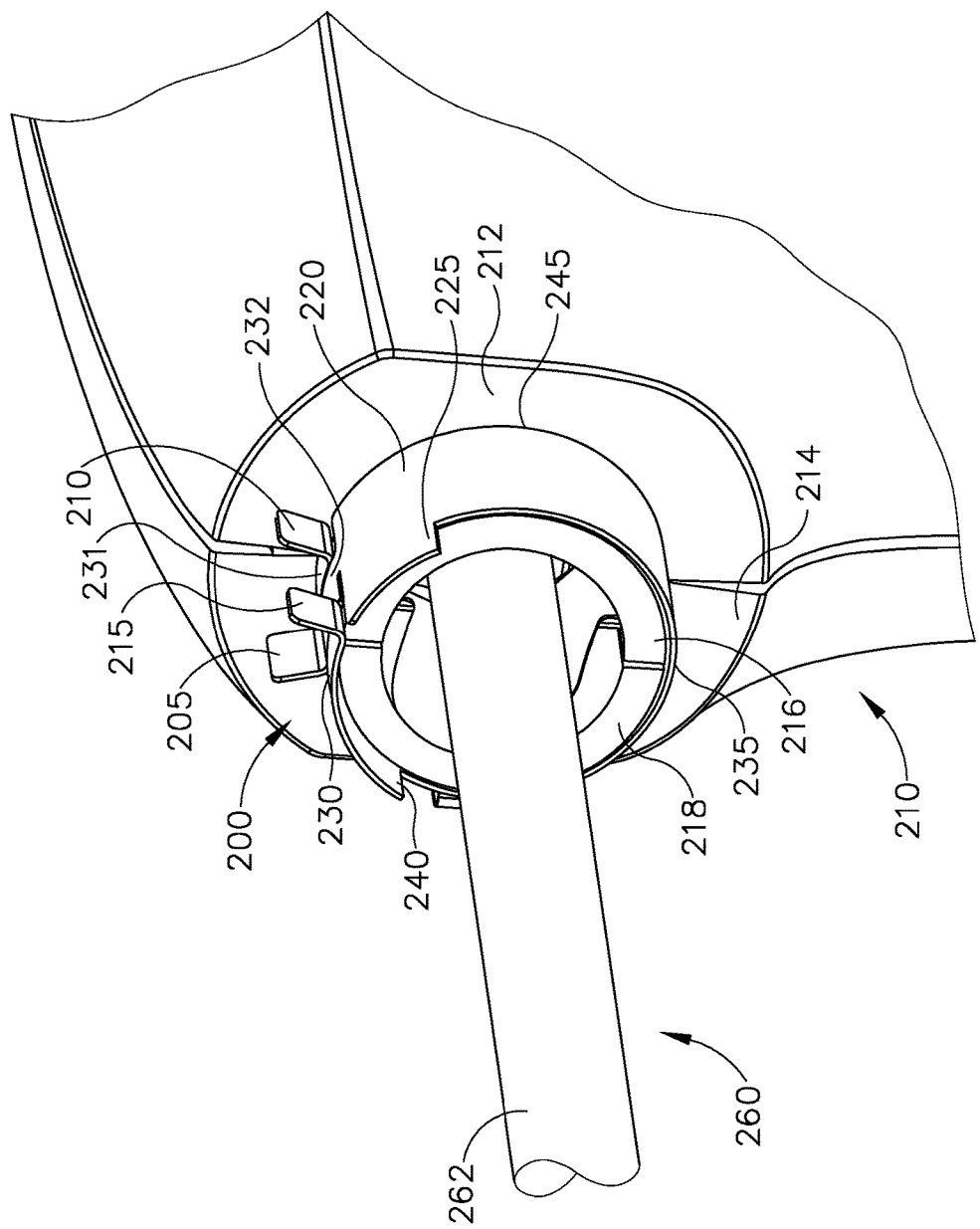
FIG. 3 depicts a perspective view of a partially assembled rotation lock feature that may be incorporated into the instrument of FIG. 1 or the instrument of FIG. 2.

One exemplary feature that may be used to prevent inadvertent rotation of end effector (40, 140) about the longitudinal axis defined by sheath (2, 132) is a spring clamp (200), as shown in FIGS. 3-6E. As best seen in FIG. 3, a shaft assembly (260) extends distally from a handle assembly (210), which comprises a pair of housing halves (212, 214). Handle assembly (210) may be configured like handle assembly (20), like handle assembly (120), or have any other suitable configuration. Each housing half (212, 214) in this example comprises a respective, distally extending boss (216, 218). Bosses (216, 218) cooperate to form an annular shape. This annular shape formed by bosses (216, 218) is concentric with shaft assembly (260). Shaft assembly (260) comprises an outer sheath (262) and a rotation knob (270), which is operable to rotate outer sheath (262) and other components of shaft assembly (260) relative to handle assembly (210) as described in greater detail below. Shaft assembly (260) may be configured like shaft assembly (30), like shaft assembly (130), or have any other suitable configuration. It should be understood that the distal end of shaft assembly (260) may include an end effector like end effector (40), an end effector like end effector (140), and/or any other suitable kind of end effector.

Spring clamp (200) comprises a resilient annular surface (220), notches (225, 240), a proximal edge (245), an offset distal edge (235), and strips (230, 231, 232) that terminate into radially extending tabs (205, 210, 215). Resilient annular surface (220) terminates on one end with single strip (232) and terminates on the other end with two strips (230, 231). Two strips (230, 231) form a U-shaped pathway that is configured to receive single strip (232). The resilient properties of spring clamp (200) ensure that single strip (232) and two strips (230, 231) angularly overlap toward each other in such a way as to conform to bosses (216, 218). In other words, spring clamp (230) is resiliently biased in a first position where interior of resilient annular surface (220) engages bosses (216, 218) in such a way that spring clamp (230) and bosses (216, 218) are fixed relative to one another in the first position. Proximal edge (245) is positioned against handle housing halves (212, 214) while offset distal edge (235) aligns flush with the distal ends of bosses (216, 218). Notches (225, 240) extend longitudinally past bosses (216, 218) as best seen in FIG. 3. While notches (225, 240) are used in the current examples, other features can be implemented onto spring clamp (200) such as slots or bent tabs similar to radially extending tabs (205, 210, 215).

Figure 4:
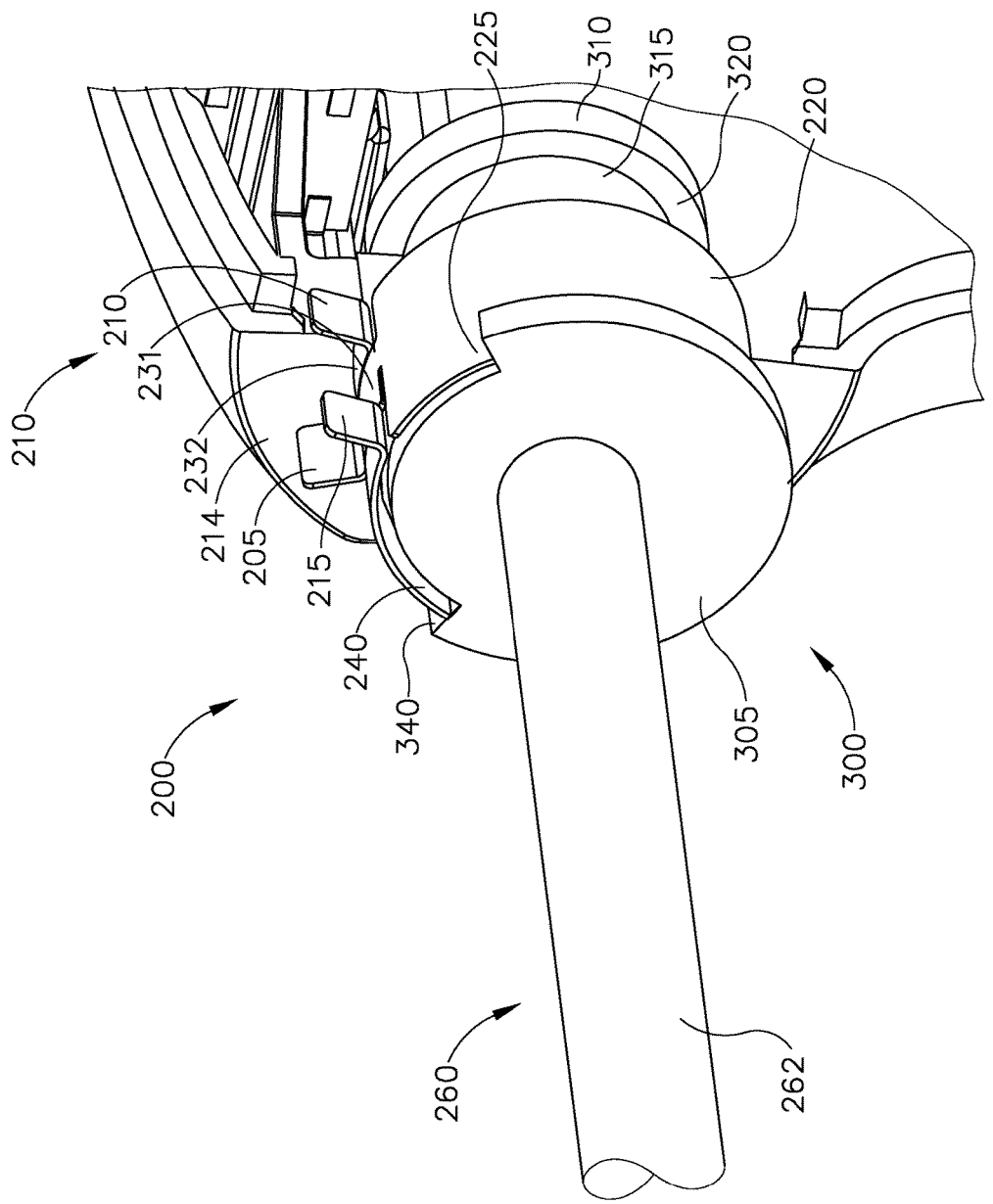
FIG. 4 depicts an enlarged perspective view of the partially assembled rotation lock feature of FIG. 3, with a housing half of the instrument handle assembly omitted.

As best seen in FIG. 4, notches (225) are in contact with a shaft retainer (300). Shaft retainer (300) is unitarily fixed to distal outer sheath (262), such that rotation of shaft retainer (300) rotates outer sheath (262) and the rest of shaft assembly (260) relative to handle assembly (210). Shaft retainer (300) comprises a proximal annular flange (210), a body (315), and a distal annular flange (305) with a cutout (340). Body (315) is dimensioned to fit within bosses (216, 218). The outer diameter of body (315) is less than the inner diameter defined by bosses (216, 218), such that shaft retainer (300) may freely rotate within bosses (216, 218) when spring clamp (200) is in an unlocked state (i.e., in the second position). Outer sheath (262) is fixedly secured within the interior of body (315). Body (315) also connects proximal annular flange (210) with distal annular flange (305). Proximal annular flange (210) further comprises contact surface (320) that is configured to engage the proximal ends of bosses (216, 218). Spring clamp (200) engages shaft retainer (300) due to contact between the outer edges of notches (225) and the inner edges of cutout (340).

Figure 5:
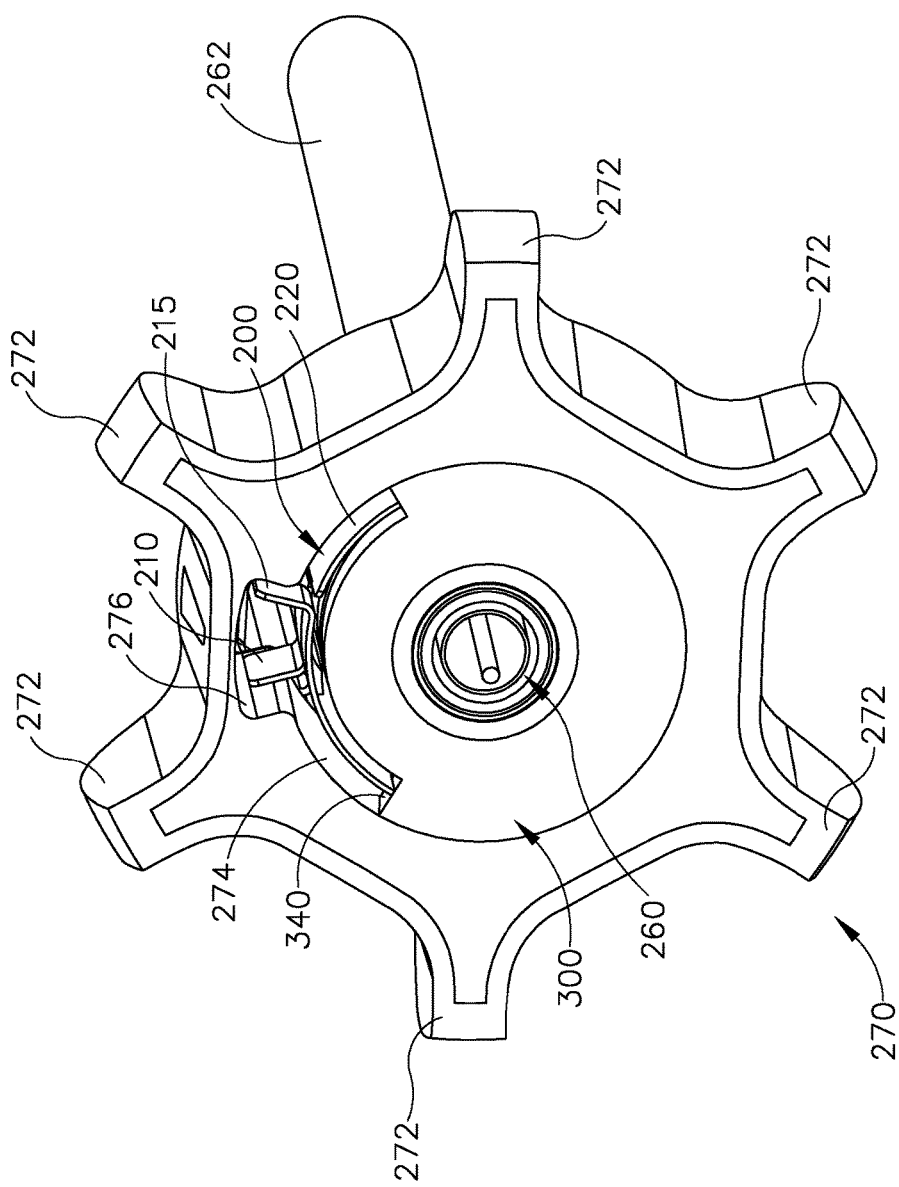
FIG. 5 depicts a perspective view of the assembled rotation lock feature of FIG. 3, positioned on a shaft assembly.

As best seen in FIG. 5, rotation knob (270) encompasses bosses (216, 218), spring clamp (200) and at least a portion of shaft retainer (300). Rotation knob (270) comprises a plurality of rotation grips (272), a rotation channel (274), and a key slot (276) extending from a portion of rotation channel (274). Rotation channel (274) forms a recess that encompasses bosses (216, 218), a portion of spring clamp (200), and a portion of shaft retainer (300). Key slot (276) provides additional space for radially extending tabs (205, 210, 215). However, rotation knob (270) is not directly in contact with shaft retainer (300) or outer sheath (262).

Therefore, rotation of knob (270) does not directly correlate to rotation of shaft assembly (260).

As described below, knob (270) is configured to interact with spring clamp (200) in order to transition spring clamp (200) from first position to a second position. When spring clamp (200) is in the first position, spring clamp (200) resiliently bears radially inwardly against bosses (216, 218), such that spring clamp (200) is effectively locked to handle assembly (210) due to a frictional braking effect. This effect is transferred to shaft assembly (260) via shaft retainer (300) due to engagement between the outer edges of notches (225) and the inner edges of cutout (340). In other words, when spring clamp (200) is in the first position, shaft retainer (300), spring clamp (200), and bosses (216, 218) all cooperate to effectively lock the rotational position of shaft assembly (260) relative to handle assembly (210). When spring clamp (200) transitions to the second position, the grip of spring clamp (200) against bosses (216, 217) is relieved, reducing or eliminating frictional braking of spring clamp (200) against bosses (216, 217), thereby allowing shaft assembly (260) to rotate relative to handle assembly (210).

The fact that spring clamp (200) transitions from the first position to the second position in response to actuation of rotation knob (270) may also provide other results. For example, if outer sheath (262) encounters incidental rotational forces due to the end effector bearing against anatomical structures of the patient during operation of the instrument in a surgical procedure, these incidental rotation forces will not cause spring clamp (200) to release. Instead, these incidental rotation forces will further tighten spring clamp (200), such that spring clamp (200) will provide further resistance to rotation of shaft assembly (260). Thus, actual rotation of knob (270) will be required in order to release spring clamp (200) to permit rotation of shaft assembly (260).

Figure 6B:
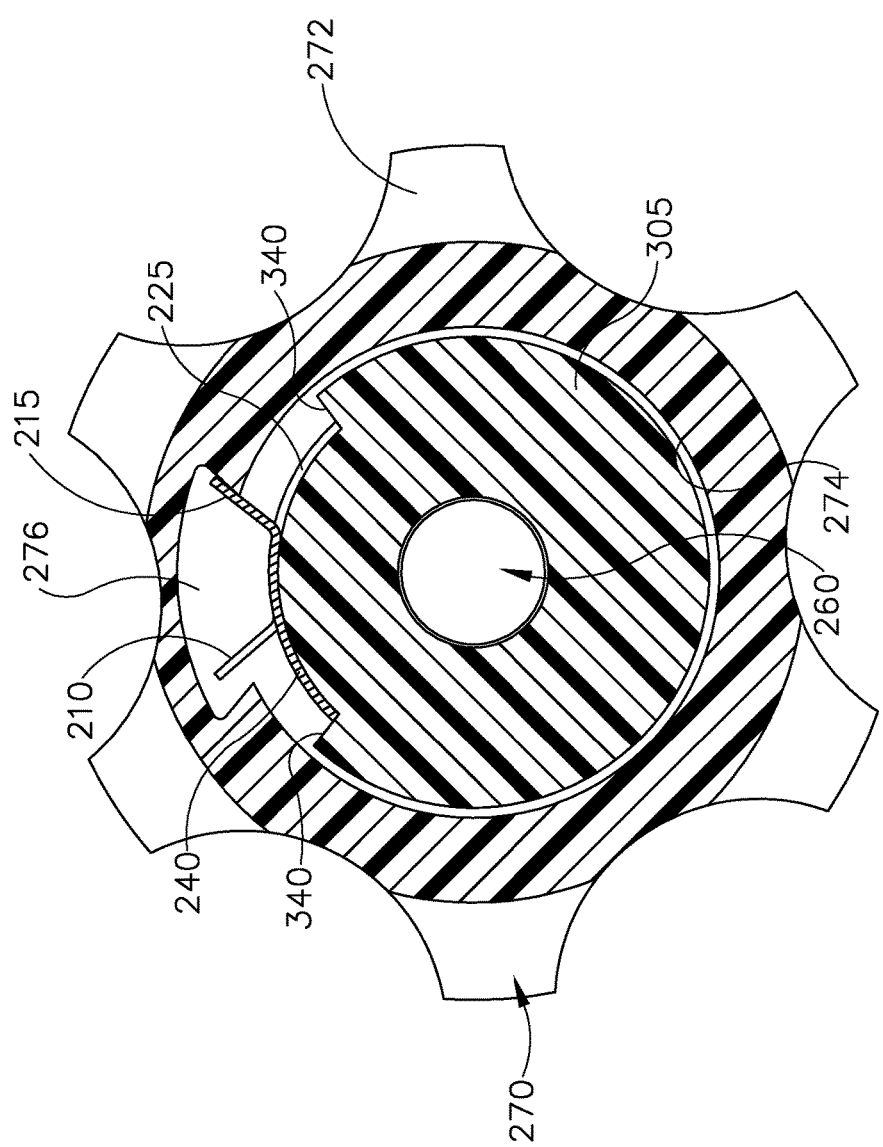
FIG. 6B depicts a cross sectional front view of the assembled rotation lock feature of FIG. 3 in an second unengaged position.

FIG. 6A shows rotation knob (270) and spring clamp (200) in a non-engaged relationship, such that tabs (205, 210, 215) are positioned within key slot (276) without engaging any interior surfaces of knob (270) that define key slot (276). At this point, spring clamp (200) is still in a first position, clamping against bosses (216, 218), thereby effectively locking the rotational position of shaft assembly (260) relative to handle assembly (210). FIG. 6B shows rotation knob (270) rotated to an angular position where an interior surface of knob (270) defining key slot (276) is in contact with radially extending tab (215), but where spring clamp (200) is still in the first position. This is the maximum amount of rotation that knob (270) is allowed without rotating shaft assembly (260) via shaft retainer (300). It should therefore be understood that there is some "play" between knob (270) and shaft assembly (260), such that there is lost motion between knob (270) and shaft assembly (260) as knob (270) is rotated through a first range of angular motion from the position shown in FIG. 6A to the position shown in FIG. 6B.

Figure 6C:
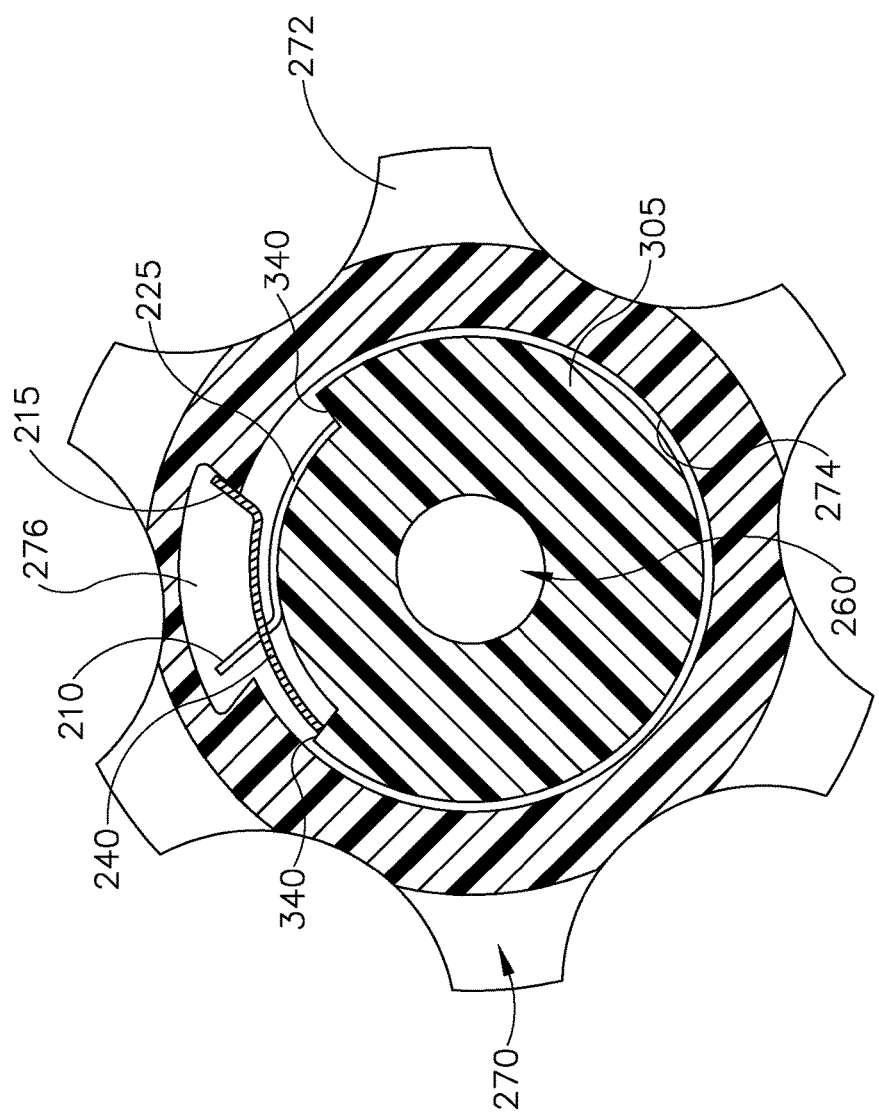
FIG. 6C depicts a cross sectional front view of the assembled rotation lock feature of FIG. 3 in a first engaged position.

FIG. 6C shows rotation knob (270) rotated further to an angular position where the surface of key slot (276) that initially contacted tab (215) at the stage shown in FIG. 6B is now bearing against tab (215) with enough force to cause spring clamp (200) to deform to the second position. As noted above, when spring clamp (200) is in the second position, spring clamp (200) the braking force of spring clamp (200) against bosses (216, 218) is substantially relieved such that spring clamp (200) may be rotated relative to bosses (216, 218). Therefore, as seen in the transition from the stage shown in FIG. 6C to the stage shown in FIG. 6D, further rotation of knob (270) provides rotation of spring clamp (200) about bosses (216, 218). Additionally, since notches (225, 240) are in direct contact with cutouts (340) of distal annular flange (305), rotation of spring clamp (200) also rotates shaft retainer (300), thereby rotating shaft assembly (260) (and the end effector (not shown) at the distal end of shaft assembly (260)). In other words, as key slot (276) of rotation knob (270) engages radially extending tab (215) of spring clamp (200), spring clamp (200) becomes free to rotate relative to handle housing halves (212, 214) while simultaneously rotating shaft assembly (260) due to contact between spring clamp (200) and shaft retainer (300).

Figure 6D:
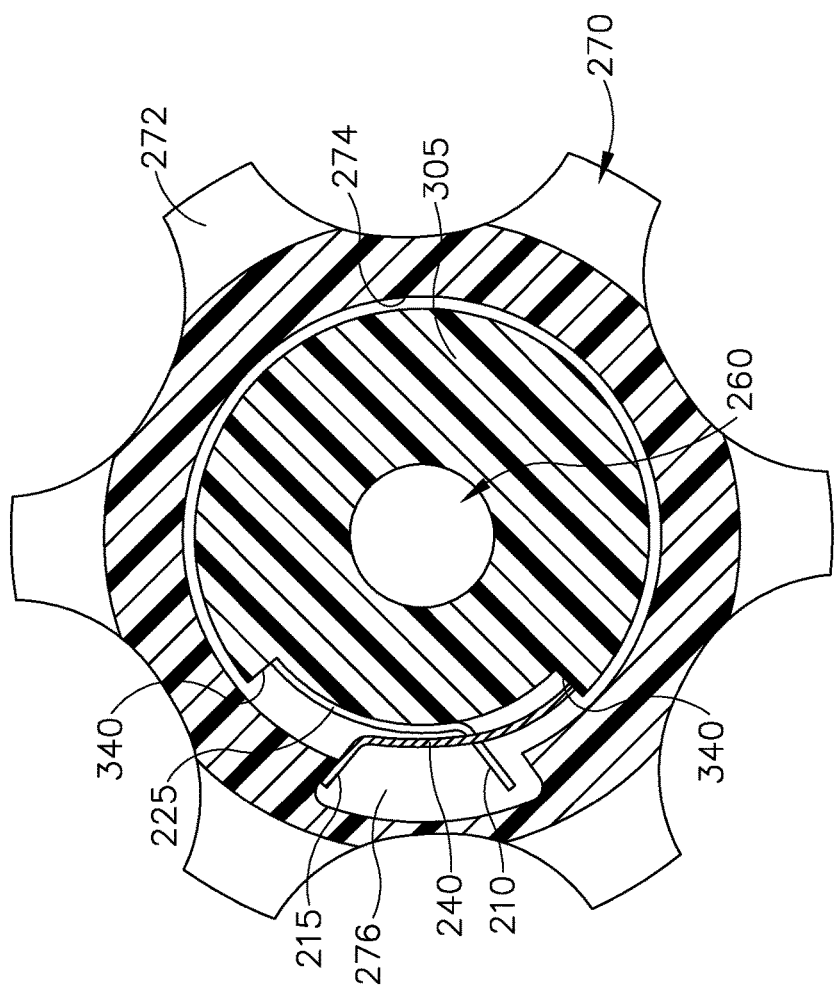
FIG. 6D depicts a cross sectional front view of the assembled rotation lock feature of FIG. 3 in a second engaged position and rotated 90 degrees.

As seen in the transition from the stage shown in FIG. 6C to the stage shown in FIG. 6D, once the operator has rotated knob (270) to orient shaft assembly (260) at the desired angular position, the operator then release knob (270). When the operator releases knob (270), the resilient properties of spring clamp (200) pushes spring clamp from the second position back to the first position. Spring clamp (200) is then agaom rotationally fixed relative to bosses (216, 218), thereby effectively locking the rotational position of shaft assembly (260) relative to handle assembly (210). While FIG. 6A depict rotation of knob (270) and shaft assembly (260) in just one angular direction, it should be understood that the above described components will operate in the same fashion when knob (270) and shaft assembly (260) are rotated in the opposite angular direction.

FIGS. 3-6E show spring clamp (200) in a flat spring form. However, spring clamp (200) may take a variety of alternative forms such as a round wire form. Additionally, spring clamp (200) can have other features for engaging key slot (276) instead of radially extending tabs (205, 210, 215). Additionally, it is not necessary for spring clamp (200) to comprise two strips (230, 231) in order to form a U-shaped pathway and angularly overlap toward single strip (232). For instance, two strips (230, 231) could be a single strip that does not overlap single strip (232) of the present example. In some such versions, a boss could be inserted on knob (270) instead of key slot (276) to engage either strip. Various suitable alternative configurations and relationships for spring clamp (200) and knob (270) will be apparent to those of ordinary skill in the art in view of the teachings herein.

B. Exemplary Trigger-Driven Clutching Lock for Shaft Assembly

Figure 7A:
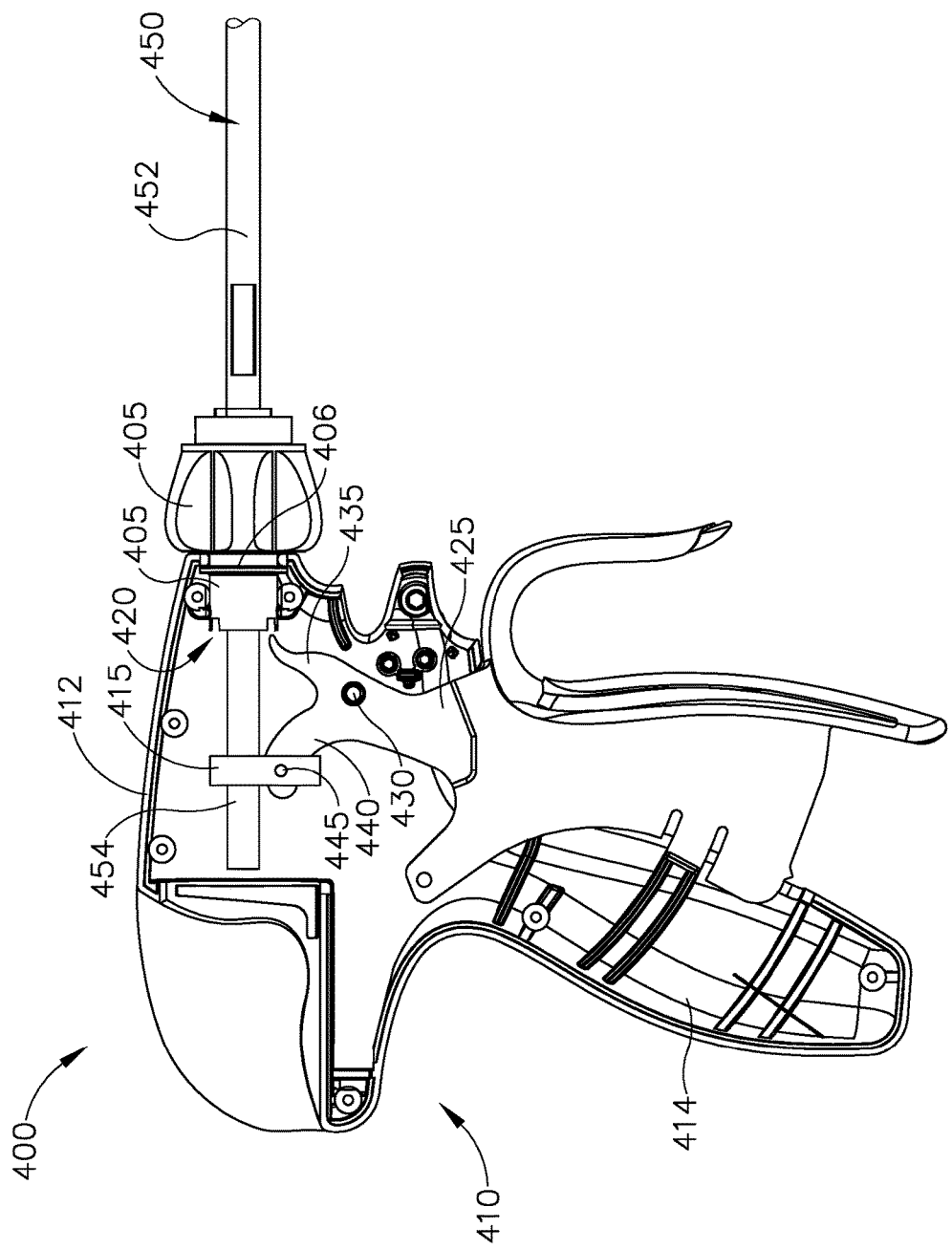
FIG. 7A depicts a side elevational view of another exemplary alternative surgical instrument, with a partially assembled rotation lock feature in an unlocked position.
Figure 7B:
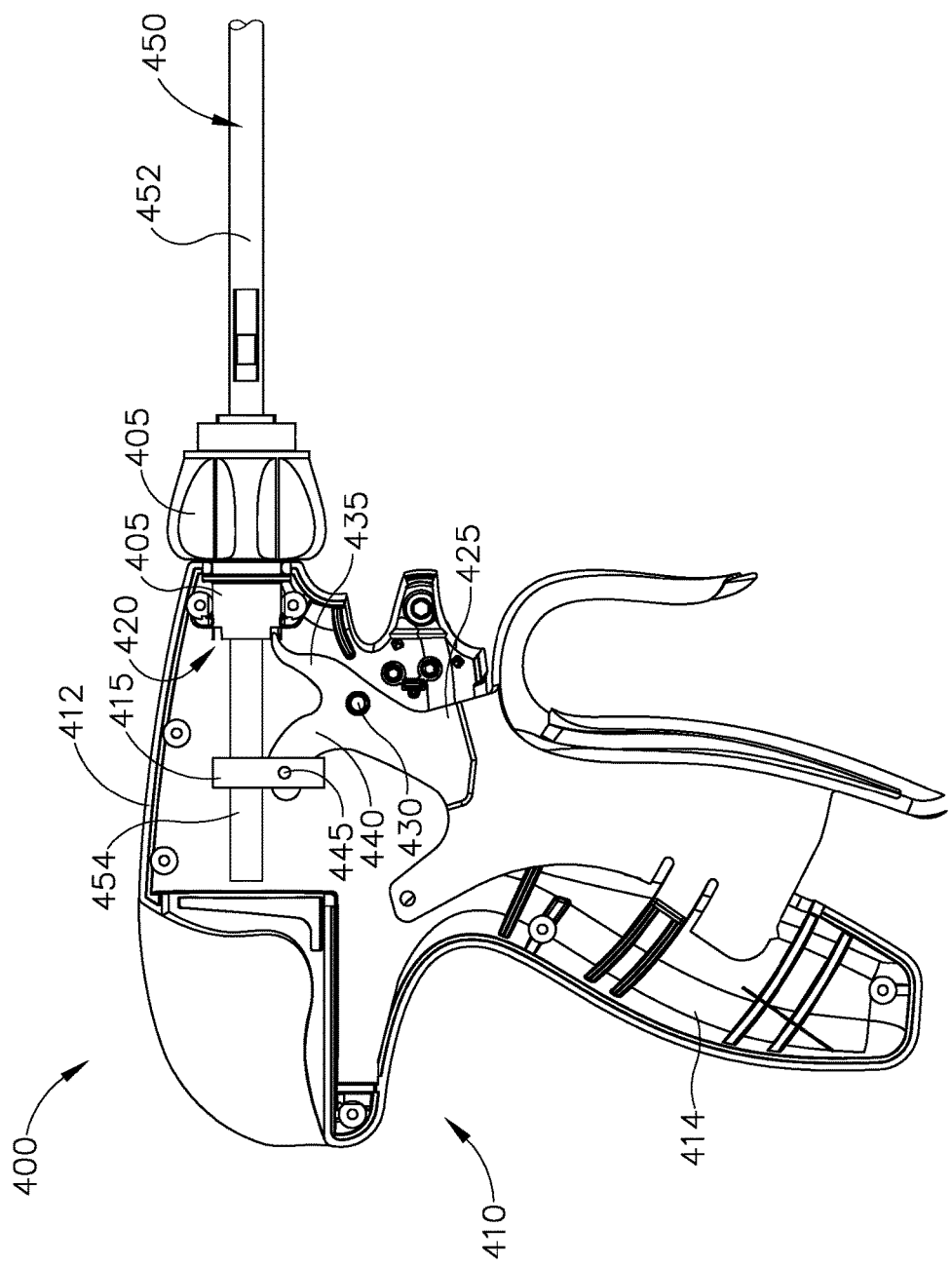
FIG. 7B depicts a side elevational view of the instrument of FIG. 7A, with the partially assembled rotation lock feature in a locked position.

In some circumstances, it may be desirable to tie the locking of the angular position of shaft assembly (30, 130) to some other operation of instrument (10, 100). For instance, it may be desirable to lock rotation of shaft assembly (30, 130) relative to handle assembly (20, 120) when trigger (28, 128) is being actuated; yet permit shaft assembly (30, 130) to be rotated relative to handle assembly (20, 120) when trigger (28, 128) is not being actuated. FIGS. 7A-7B show an exemplary instrument (400) that is configured to provide such functionality.

Instrument (400) of the present example comprises a handle assembly (410) and a shaft assembly (450). Handle assembly (410) comprises a housing (412), a pistol grip (414), and a trigger (425) that is pivotable toward and away from pistol grip (414). It should be understood that handle assembly (410) may further include any of the other features of handle assembly (20), any of the other features of handle assembly (120), and/or any other suitable features. Shaft assembly (450) is selectively rotatable relative to handle assembly (410) as will be described in greater detail below. Shaft assembly (450) comprises an outer sheath (452) and an inner tubular actuating member (454). Inner tubular actuating member (454) is configured to translate within outer sheath (452) to thereby actuate an element of an end effector (450) at the distal end of shaft assembly. For instance, such an element may be similar to clamp arm (44) or second jaw (144). It should therefore be understood that the distal end of shaft assembly (450) may include an end effector like end effector (40), an end effector like end effector (140), and/or any other suitable kind of end effector. Moreover, shaft assembly (450) may be configured like shaft assembly (30), like shaft assembly (130), or have any other suitable configuration.

Instrument (400) further includes a rotation knob (405), which is fixedly secured to outer sheath (452). Rotation knob (405) is rotatably supported by housing (412) of handle assembly (410) via an annular flange (406). In particular, housing (412) supports rotation knob (405) via flange (406) while still permitting rotation knob (405) to rotate via flange (406). The proximal end of rotation knob (405) includes an angular array of proximally presented locking recesses (420), which will be described in greater detail below. When rotation knob (405) is in an unlocked state, the operator may grasp rotation knob (405) and rotate shaft assembly (450) relative to handle assembly (410) via rotation knob (405). When rotation knob (405) is in a locked state, shaft assembly (450) cannot be rotated relative to handle assembly (410).

Trigger (425) is pivotably mounted to housing (410) via a pin (430). Trigger (425) further comprises an actuating arm (440) and a locking arm (435). Actuating arm (440) is coupled to an actuating collar (415) via pin (445). Actuating collar (415) is fixed to inner tubular actuating member (454). Therefore, closure of trigger (425) toward pistol grip (414) rotates actuating arm (440) via pin (430), which in turn translates actuating collar (415) and inner tubular actuating member (454) distally. Additionally, locking arm (435) pivots about pin (430) in response to closure of trigger (425).

Figure 8A:
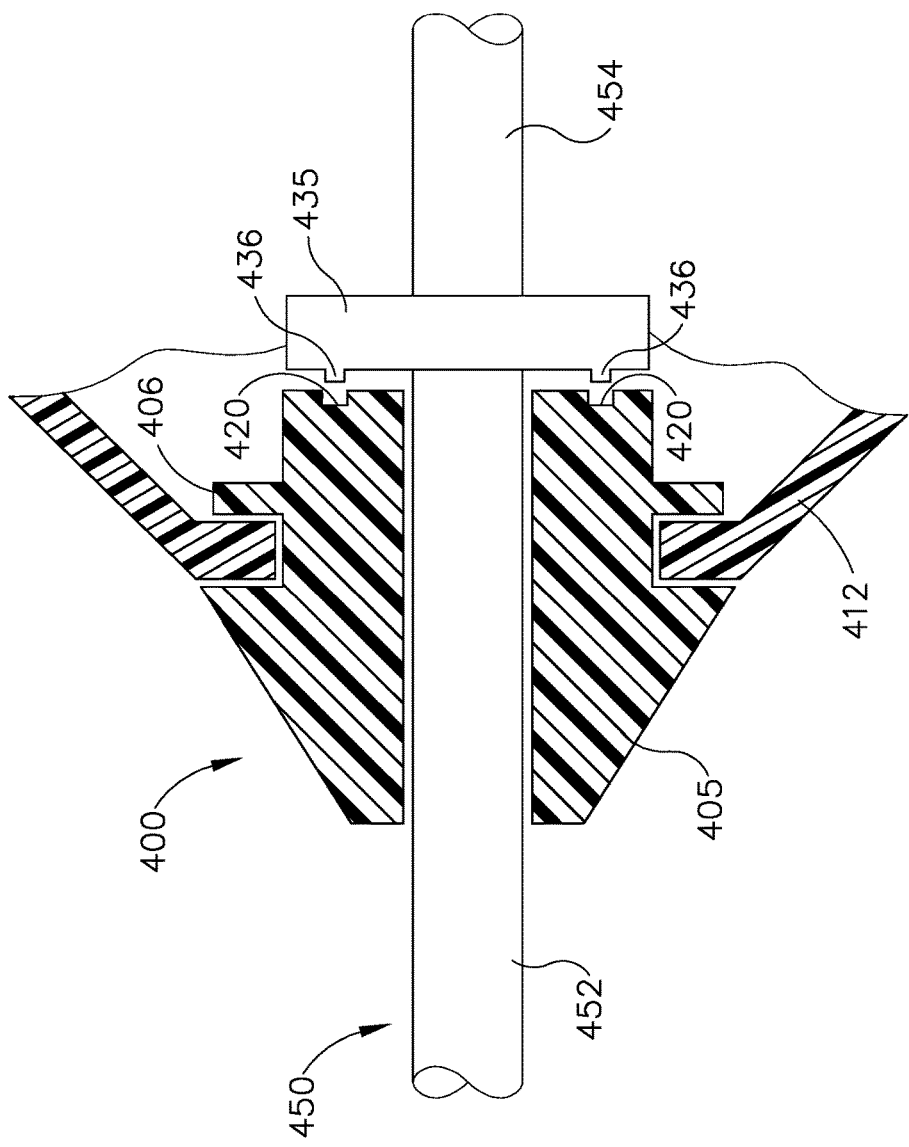
FIG. 8A depicts a top cross-sectional view of the instrument of FIG. 7A, with the rotation lock feature in the unlocked position.
Figure 8B:
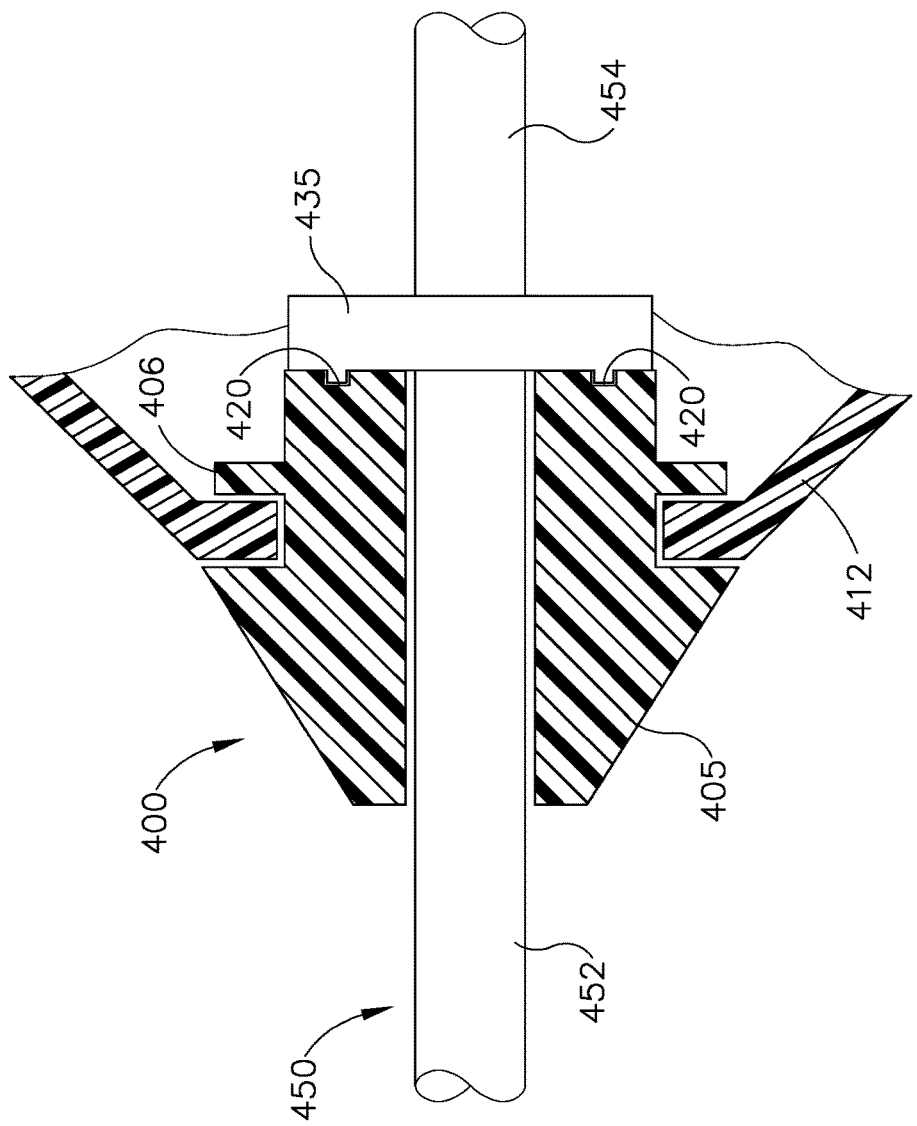
FIG. 8B depicts a top cross-sectional view of the instrument of FIG. 7A, with the rotation lock feature in the locked position.

As best seen in FIGS. 8A-8B, locking arm (435) includes a pair of distally oriented projections (436) that are positioned to selectively engage locking recesses (420) of knob (405). In particular, when trigger (425) is in the relaxed state as shown in FIGS. 7A and 8A, projections (436) are spaced away from recesses (420), With projections (436) being spaced away from recesses (420), knob (405) and shaft assembly (450) are free to rotate relative to handle assembly (410). It should also be understood that the movable element of the end effector that is coupled with inner tubular actuating member (454) will be in a non-actuated state when trigger (425) is in the relaxed state as shown in FIGS. 7A and 8A. When trigger (425) is pivoted toward pistol grip (414), trigger (452) reaches the position shown in FIGS. 7B and 8B. At this stage, inner tubular actuating member (454) is advanced distally via actuating collar (415), thereby actuating he movable element of the end effector that is coupled with inner tubular actuating member (454). In addition, locking arm (435) is pivoted to a position where projections (436) are received in recesses (420). The engagement of projections (436) in recesses (420) will effectively lock knob (405) such that knob (405) and shaft assembly (450) are prevented from rotating relative to handle assembly (410) when trigger (425) is in the actuated position shown in FIGS. 7B and 8B. When the operator releases trigger (425), instrument (400) returns back to the state shown in FIGS. 7A and 8A. It should therefore be understood that the instrument (400) prevents rotation of shaft assembly (450) relative to handle assembly (410) when a movable element of the end effector is being actuated; yet permits rotation of shaft assembly (450) relative to handle assembly (410) when the movable element of the end effector is not being actuated.

In some versions, locking arm (435) is deformable in the plane along which trigger (425) pivots; yet is substantially non-deformable along a path that is transverse to the pivot plane. For instance, locking arm (435) may be configured such that projections (436) are received in recesses (420) as soon as trigger (425) pivots through a first range of motion toward pistol grip (414); and such that locking arm (435) deforms (with projections (436) still being received in recesses (420)) as trigger (425) pivots through a second range of motion toward pistol grip (414). In some such versions, trigger (425) does not complete the actuation of the movable element of the end effector until trigger (425) completes the second range of motion. Thus, locking arm (435) may prevent rotation of shaft assembly (450) relative to handle assembly (410) before the movable element of the end effector is fully actuated. Locking arm (435) may be configured such that projections (436) engage recesses (420) to prevent rotation of shaft assembly (450) relative to handle assembly (410) at any suitable stage of actuation of the movable element of the end effector.

In some other variations, locking arm (435) is pivotably mounted to trigger (425), such that locking arm (435) pivots relative to trigger (425) as trigger (425) pivots through the second range of motion relative to pistol grip (414). In some such versions, a resilient member may bias locking arm (435) to engage recesses (420) as soon as trigger (425) pivots through the first range of motion toward pistol grip (414). Other suitable configurations for locking arm (435) will be apparent to those of ordinary skill in the art in view of the teachings herein. Similarly, other suitable relationships between trigger (425) and locking arm (435) will be apparent to those of ordinary skill in the art in view of the teachings herein. As yet another merely illustrative alternative, locking arm (4350 may be omitted, and projections (436) may be secured to actuating collar (415) or inner tubular actuating member (454). In versions where projections (436) are secured to inner tubular actuating member (454), projections (456) may be incorporated into a locking collar that is fixedly secured to inner tubular actuating member (454).

Since knob (405) has a finite number of recesses (420), there may be occasions where the operator actuates trigger (425) when projections (436) are not perfectly angularly aligned with corresponding recesses (420). Thus, projections (436) and/or recesses (420) may include obliquely angled cam features, curved cam features, and/or other kinds of features that are configured to provide self-alignment to thereby fully seat projections (436) in recesses (420). In other words, such self-alignment features may provide whatever further minimal rotation of shaft assembly (450) that might be necessary in order to fully seat projections (436) in recesses (420) as trigger (425) completes a range of pivotal motion toward pistol grip (414). In such versions, it may be desirable to maximize the number of recesses (420) in order to minimize the amount of further rotation that might be required in order for self-alignment features to fully seat projections (436) in recesses (420). Minimizing the amount of further rotation that is required in order to fully seat projections (436) in recesses (420) may minimize the risk of operator frustration, as it will make the final angular orientation of shaft assembly (450) as close as possible to the angular orientation selected by the operator.

C. Exemplary Cam-Driven Clutching Lock for Shaft Assembly

Figure 9A:
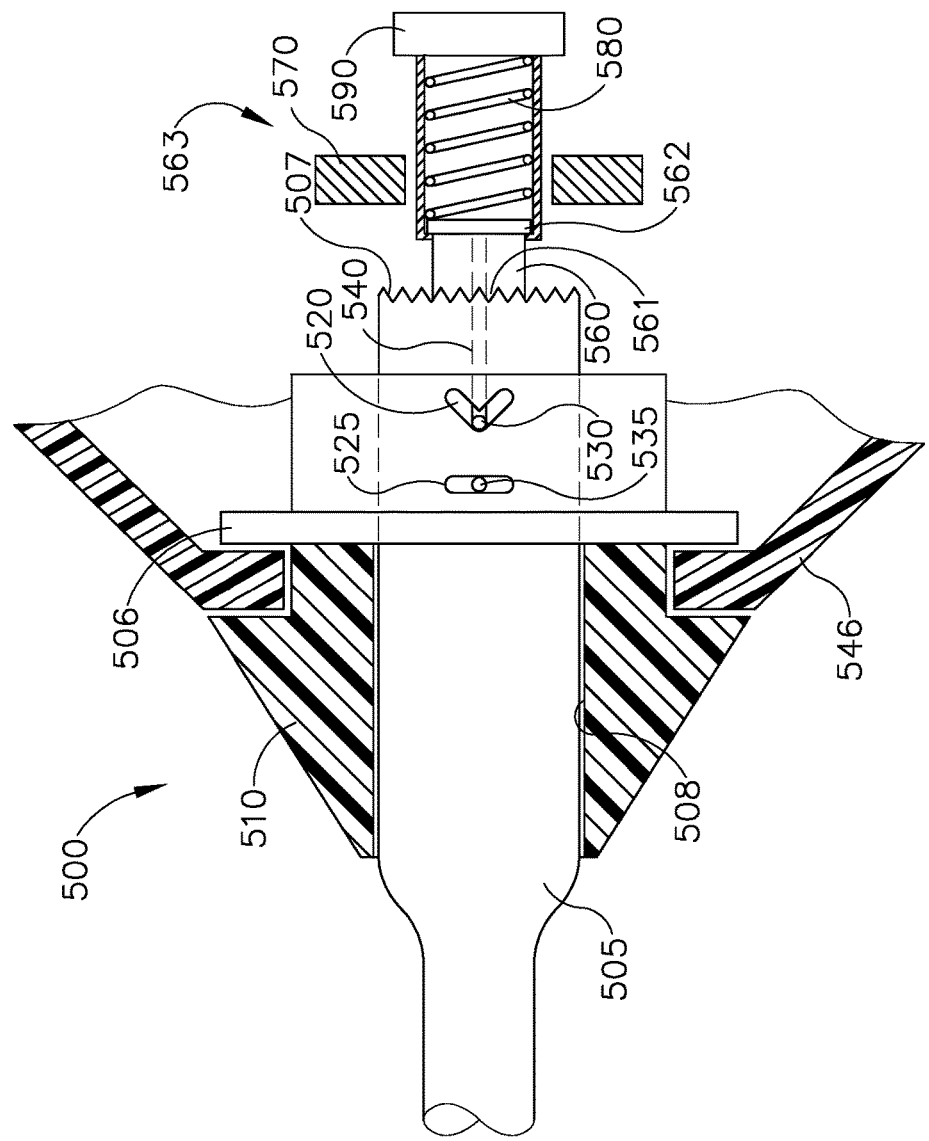
FIG. 9A depicts a top cross-sectional view of a partially assembled exemplary alternative rotation lock feature that may be incorporated into the instrument of FIG. 1 or the instrument of FIG. 2, with the rotation lock feature in an unlocked position.
Figure 9B:
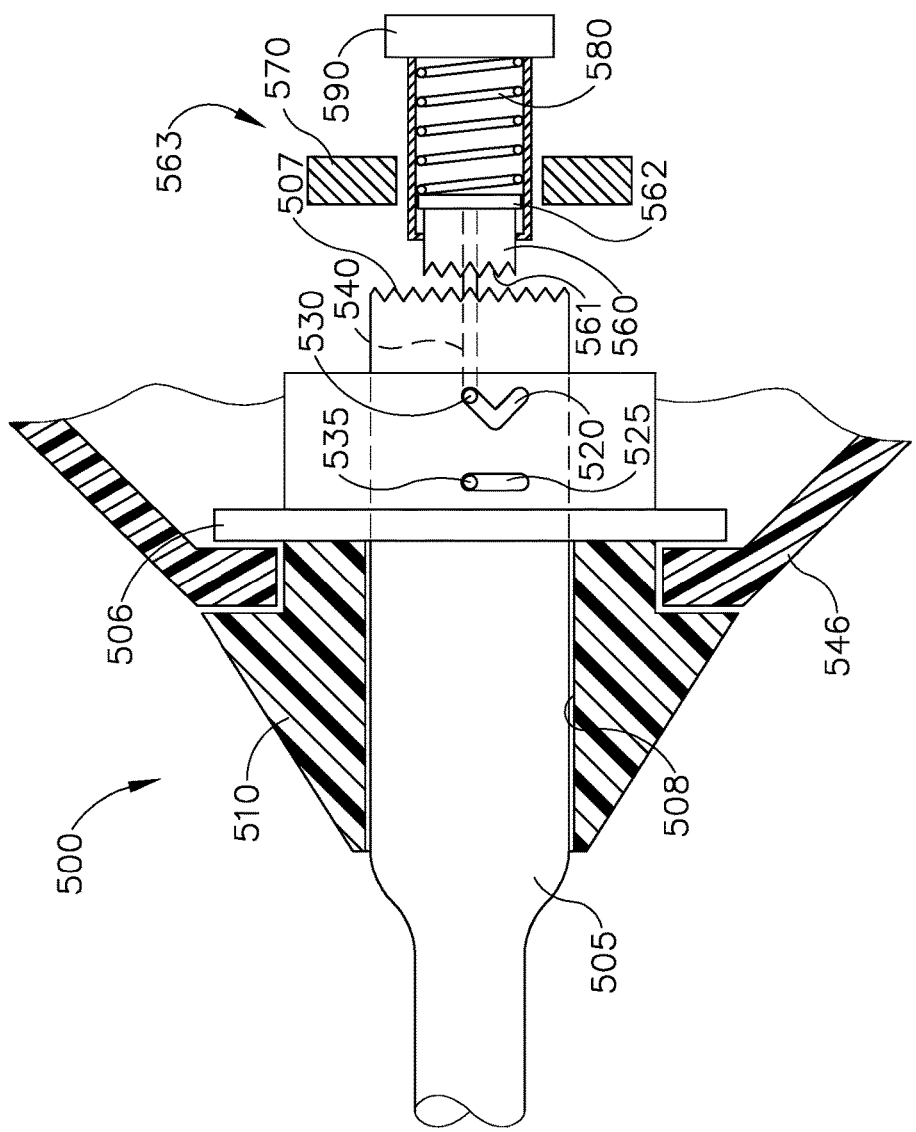
FIG. 9B depicts top cross-sectional view of the partially assembled rotation lock feature of FIG. 9A in a locked position.

In some instances, it may be desirable to lock rotation of shaft assembly (30, 130) relative to handle assembly (20, 120) whenever the operator is not attempting to rotate knob (34, 134); and to only unlock rotation of shaft assembly (30, 130) relative to handle assembly (20, 120) when the operator is actively rotating knob (34, 134). To that end, FIGS. 9A-9B show a locking mechanism (500) comprising a rotation knob (510), and a biased locking member (563). Rotation knob (510) is secured to a shaft assembly (505) and is thereby operable to selectively rotate shaft assembly (505) relative to a handle assembly (546). It should be understood that handle assembly (546) may further include any of the other features of handle assembly (20), any of the other features of handle assembly (120), and/or any other suitable features. Shaft assembly (505) may be configured like shaft assembly (30), like shaft assembly (130), or have any other suitable configuration. Moreover, the distal end of shaft assembly (505) may include an end effector like end effector (40), an end effector like end effector (140), and/or any other suitable kind of end effector.

Rotation knob (510) is rotatably supported by handle assembly (546) via an annular flange (506). In particular, handle assembly (546) supports rotation knob (510) via flange (506) while still permitting rotation knob (510) to rotate via flange (506). Rotation knob (510) further comprises a channel (508), a linear slot (525), and a V-shaped slot (520). V-shaped slot (520) includes a pair of obliquely angled slot legs. It should be understood that slot (520) may have various other suitable configurations, such that a "V" shape is not necessary. Other suitable shapes that slot (520) may have will be apparent to those of ordinary skill in the art in view of the teachings herein.

A proximal portion of shaft assembly (505) that protrudes proximally from knob (510) comprises an annular array of proximally oriented teeth (507). Shaft assembly (505) further includes transversely oriented pin (535) that is received in linear slot (525) of rotation knob (510). Biased locking member (563) further comprises a fixed member (590), a resilient member (580), a guide channel (570), a rotation lock base (562), a rotation lock body (560), a rotation lock shaft (540), and a rotation lock pin (530). Rotation lock body (560) further comprises a set of distally oriented lock teeth (561) that are configured to selectively engage teeth (507) of shaft assembly (505).

One end of resilient member (580) is engaged with fixed member (590), while the other end of resilient member (580) is engaged with lock base (562). Fixed member (590) is fixedly secured to handle assembly (546). Resilient member (580) is configured to resiliently bias lock base (562) distally. In the present example, resilient member (580) comprises a coil spring, though it should be understood that any other suitable kind of resilient member may be used. Guide channel (570) ensures that resilient member (580) is facing the appropriate direction, preventing resilient member (580) from buckling laterally or otherwise deviating from a path that is parallel to the longitudinal axis of shaft assembly (505).

Rotation lock body (560) is secured to lock base (562), such that resilient member (580) biases rotation lock body (560) distally via lock base (562). Rotation lock body (560) and lock base (562) are configured to translate within handle assembly (546) but are prevented from rotating within handle assembly (546). For instance, rotation lock body (560) and/or lock base (562) may be engaged with handle assembly (546) via a complementary key and keyway. As another merely illustrative example, rotation lock body (560) and/or lock base (562) may have a non-circular cross-sectional profile that is received in a complementary recess or other mounting structure in handle assembly (546). Other suitable configurations will be apparent to those of ordinary skill in the art in view of the teachings herein.

The proximal end of rotation lock shaft (540) is engaged with lock base (562) such that lock shaft (540) and lock base (562) translate with each other relative to handle assembly (546). However, unlike lock base (562), lock shaft (540) is configured to rotate relative to handle assembly (546) once lock shaft (540) has reached a fully proximal position in an unlocked state, as described in greater detail below. The distal end of lock shaft (540) includes a transversely oriented pin (530), which is disposed within V-shaped slot (520). Various suitable ways in which lock shaft (540) may coupled with lock base (562) in order to provide such functionality will be apparent to those of ordinary skill in the art in view of the teachings herein. For example, fins/pins could be implemented on lock shaft (540) or pin (530), where fins/pins are configured to interface with short grooves in any fixed element, such as handle assembly (546), guide channel (570) or fixed member (590). Additionally, fins/pins do not necessarily need to be implemented on lock shaft (540), as lock shaft (540) could be fixed to lock base (562) or lock body (560), in which lock base (562) or lock body (560) could have fins/pins configured to rotate lock base (562) or lock body (560) once fully proximal, but limiting rotation in a distal position.

FIG. 9A shows locking mechanism (500) in a locked state. In this state, resilient member (580) urges lock body (560) to a distal position, such that teeth (561) are engaged with teeth (507). Pin (530) is positioned at the vertex of the angle defined by the oblique legs of slot (520). With teeth (561, 507) engaged, lock body (560) prevents shaft assembly (505) from rotating relative to handle assembly (546). When in a locked state, lock shaft (540) is configured to only translate, so when the operator rotates knob (510) relative to handle assembly (546), V-shaped slot (520) provides a camming action against pin (530), driving lock body (560) proximally via lock shaft (540). This moves lock body (560) to a proximal position as shown in FIG. 9B, where teeth (561) are disengaged from teeth (507). With teeth (561, 507) disengaged, locking mechanism (500) is now in an unlocked state. When locking mechanism (500) is in an unlocked state, shaft assembly (505) is now rotatable relative to handle assembly (546). Additionally, as mentioned above, when locking mechanism (500) is in an unlocked state, lock shaft (540) is now free to rotate relative to lock base (562). It should be noted that, at this stage of operation, pin (535) of shaft assembly (505) has reached the end of slot (525). Thus, further rotation of knob (510) will cause shaft assembly (505) to rotate due to engagement between pin (535) and the end of slot (525). Pin (535) does not reach the end of slot (525) until locking mechanism (500) has reached the unlocked state shown in FIG. 9B.

Once the operator has achieved the desired rotational position of shaft assembly (505), the operator may simply release knob (510). When the operator releases knob (510), the bias of resilient member (580) will urge lock base (562) and lock body (560) back to the distal position shown in FIG. 9A, such that teeth (561, 507) will be reengaged to lock the adjusted rotational position of shaft assembly (505) relative to handle assembly (546). Pin (530) will provide a camming action against slot (525), rotating knob (510) as pin (530) and lock shaft (540) travel distally until pin (530) again reaches the apex of V-shaped slot (520) as also shown in FIG. 9A. Locking mechanism (500) will thus automatically transition back to the locked state after the operator releases knob (510).

D. Exemplary Knob-Driven Braking Lock for Shaft Assembly

Figure 10A:
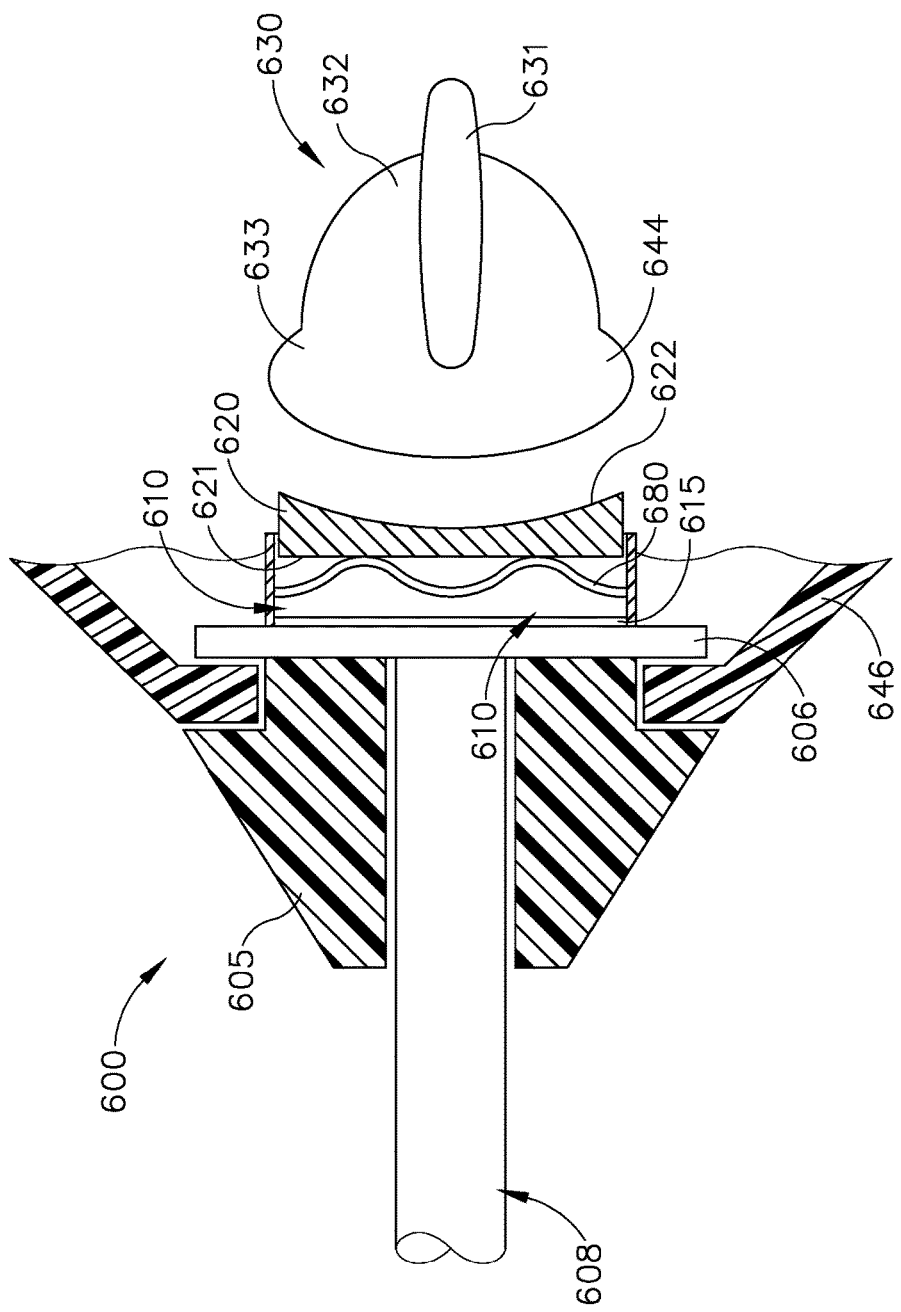
FIG. 10A depicts a top cross-sectional view of a partially assembled exemplary alternative rotation lock feature that may be incorporated into the instrument of FIG. 1 or the instrument of FIG. 2, with the rotation lock feature in an unlocked position.
Figure 10B:
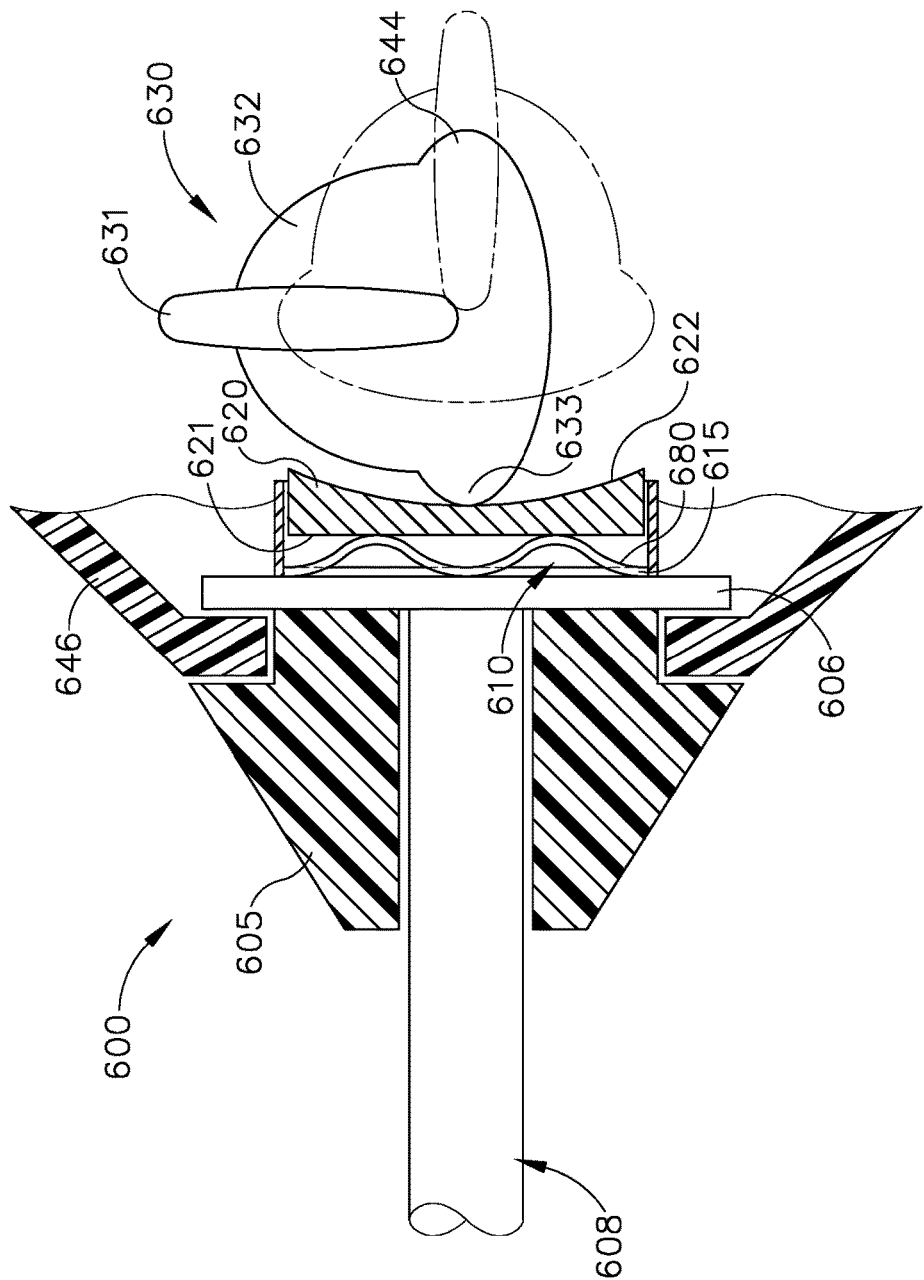
FIG. 10B depicts top cross-sectional view of the partially assembled rotation lock feature of FIG. 10A in a locked position.

In some instances, it may be desirable to provide a separate, dedicated input feature for the operator to selectively lock and unlock rotation of shaft assembly (30, 130) relative to handle assembly (20, 120). To that end, FIGS. 10A-10B show an exemplary locking mechanism (600) comprising a rotation knob (605), a bearing washer (615), a wave spring (680), a cam interface plate (620), and a locking knob (630). Locking knob (630) is rotatably fixed to body (646). Locking feature comprises a locking arm (631), and a locking body (632) with a pair of cam lobes (622, 633). Cam interface plate (620) further comprises a concave surface (622) facing locking knob (630) and a flat surface facing wave spring (680).

Rotation knob (605) is secured to shaft assembly (608) such that rotation knob (605) is operable to rotate shaft assembly (608) relative to handle assembly (646). It should be understood that handle assembly (646) may further include any of the other features of handle assembly (20), any of the other features of handle assembly (120), and/or any other suitable features. Shaft assembly (608) may be configured like shaft assembly (30), like shaft assembly (130), or have any other suitable configuration. Moreover, the distal end of shaft assembly (608) may include an end effector like end effector (40), an end effector like end effector (140), and/or any other suitable kind of end effector.

Rotation knob (605) further comprises an annular flange (606) and a wave spring channel (610). Bearing washer (615) is placed in between flange (606) and wave spring (680), within wave spring channel (610). Rotation knob (605) is rotatably supported by handle assembly (646) via annular flange (606). In particular, handle assembly (646) supports rotation knob (605) via flange (606) while still permitting rotation knob (605) to rotate via flange (606).

The operator may selectively rotate knob (630) in order to selectively prevent or permit rotation of shaft assembly (608) relative to handle assembly (646). In particular, FIG. 10A shows locking mechanism (600) in an unlocked state. In this state, wave spring (680) is not being compressed against bearing washer (615), such that shaft assembly is not encountering any substantial resistance to rotation relative to handle assembly (646). When the operator rotates knob (630) to transition locking mechanism to a locked state shown in FIG. 10B, cam lobe (633) bears against cam interface plate (620), driving cam interface plate (620) distally. This in turn compresses wave spring (680) against bearing washer (615), generating a frictional braking effect against flange (606) via bearing washer (615). This effectively locks rotation of shaft assembly (608) relative to handle assembly (646). When the operator wishes to again rotate shaft assembly (608) relative to handle assembly (646), the operator may rotate knob (630) back to the position shown in FIG. 10A, thereby transitioning locking mechanism (600) back to the unlocked state.

It should be understood that either cam lobe (633) or cam lobe (644) may be used to drive cam interface plate (620) distally, depending on the direction in which knob (630) is rotated. In some other versions, knob (630) is only rotatable in one direction to selectively lock rotation of shaft assembly (608) relative to handle assembly (646). Thus, one of cam lobes (633, 644) may be omitted. It should also be understood that wave spring (680) may be omitted. For instance, cam interface plate (620) may be positioned and configured to bear directly against bearing washer (615). In some variations, locking mechanism (600) relies on selective engagement between teeth at the distal face of cam interface plate (620) and at the proximal face of knob (605) in order to provide selective locking, in a manner similar to locking mechanism (500). It should also be understood that while knob (630) can act as a manual input to lock and unlock rotation of shaft assembly (608), knob (630) could also be configured to provide additional action, including but not limited to driving articulation of an articulation section in shaft assembly (608). Still other suitable variations will be apparent to those of ordinary skill in the art in view of the teachings herein.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a body assembly; (b) a shaft comprising a proximal end, and a distal end, wherein the shaft extends distally from the body assembly, wherein the shaft defines a longitudinal axis; (c) an end effector positioned at the distal end of the shaft; (d) a rotation input feature comprising a proximal end and a distal end, wherein the rotation input feature is configured to rotate one or both of the shaft assembly or the end effector about the longitudinal axis; and (e) a locking feature configured to transition between a locked state and an unlocked state, wherein the locking feature is configured to prevent rotation of the one or both of the shaft assembly when the locking feature is in the locked state, wherein the locking feature is configured to permit rotation of the one or both of the shaft assembly when the locking feature is in the unlocked state.

Example 2

The apparatus of Example 1 or any of the following Examples, wherein the proximal end of the shaft further comprises a shaft retainer unitarily coupled to the shaft, wherein the body further comprises at least one boss extending distally from the body assembly.

Example 3

The apparatus of Example 2, wherein locking feature further comprises a spring clamp resiliently biased to surround the at least one boss.

Example 4

The apparatus of Example 3, wherein the spring clamp further comprises a set of notches extending distally from the at least one boss, wherein the shaft retainer further comprises a set of cutouts adjacent to the set of notches.

Example 5

The apparatus of Example 4, wherein the rotation input feature further comprises a rotation channel and a key slot, wherein the rotation channel is configured to house the locking feature and the shaft retainer, wherein the key slot is configured to contact the spring clamp to transition the locking feature from the locked state to the unlocked state.

Example 6

The apparatus of Example 5, wherein the set of cutouts are configured to contact the notches when the locking feature is in the unlocked state, thereby rotating the shaft.

Example 7

The apparatus of Example 3, wherein the spring clamp further comprises a plurality of tabs.

Example 8

The apparatus of Example 7, wherein the rotation input feature further comprises a key slot housing the tabs, wherein the key slot is configured to contact the tabs to transition the locking feature from the locked state to the unlocked state.

Example 9

The apparatus of Example 2, wherein the at least one boss and the shaft retainer are coaxially aligned.

Example 10

The apparatus of any of the preceding or following Examples, wherein the rotation input feature comprises a rotation knob, wherein a proximal end of the rotation knob is within the body assembly, wherein the distal end of the rotation knob extends distally from body assembly.

Example 11

The apparatus of Example 10, wherein the rotation knob further comprises an integral flange within the body assembly, wherein the retention ring is configured to maintain a longitudinal position of the rotation knob relative to the body assembly.

Example 12

The apparatus of any of the preceding or following Examples, wherein a proximal end of rotation input feature comprises one or more locking features.

Example 13

The apparatus of Example 12, further comprising a trigger movably mounted to the body assembly, wherein the end effector comprises a movable member coupled with the trigger such that the trigger is movable relative to the body assembly to move the movable member of the end effector.

Example 14

The apparatus of Example 13, wherein the trigger further comprises one or more locking features, wherein the one or more locking features of the rotation input feature are configured to cooperate with the one or more locking features of the trigger to form the locking feature, such that the one or more locking features of the trigger are configured to selectively engage the one or more locking features of the rotation input feature to thereby provide the locked state.

Example 15

The apparatus of Example 14, wherein the trigger is configured to provide engagement between the one or more locking features of the trigger and the one or more locking features of the rotation input feature as the trigger is moved to provide movement of the movable member of the end effector.

Example 16

The apparatus of any of the preceding or following Examples, wherein the rotation input feature further comprises a cam slot; wherein the shaft further comprises a set of teeth; wherein the locking feature further comprises: (i) a rotation lock having a set of teeth configured to engage the teeth of the shaft, wherein the rotation lock is resiliently biased to provide engagement between the teeth of the rotation lock and the teeth of the shaft, and (ii) a first pin disposed in the cam slot of the rotation input feature, wherein first the pin is in communication with the rotation lock, wherein the rotation input feature is rotatable to drive the first pin to thereby disengage the teeth of the rotation lock from the teeth of the shaft.

Example 17

The apparatus of Example 16, wherein the rotation input feature further comprises a linear slot, wherein the shaft further comprises a second pin inserted with the linear slot, wherein the rotation input feature is operable to rotate the shaft via the second pin.

Example 18

The apparatus of any of the preceding or following Examples, wherein the locking feature further comprises a locking body rotatably fixed within the body assembly, wherein the locking body further comprises cam surfaces configured to engage the rotation input feature to place locking feature in the locked state.

Example 19

An apparatus comprising: (a) a body assembly; (b) a shaft assembly, wherein the shaft assembly extends distally from the body assembly, wherein the shaft assembly defines a longitudinal axis, wherein the shaft assembly further comprises: (i) an external sheath, and (ii) an internal actuation member located with the sheath; (c) an end effector located at a distal end of the shaft assembly, wherein the end effector includes a movable member coupled with the internal actuation member of the shaft assembly; (d) a rotation knob secured to the external sheath, wherein the rotation knob comprises a proximal end and a distal end, wherein the rotation knob is configured to rotate the end effector about the longitudinal axis; (e) an actuator configured to move relative to the body assembly to thereby move the internal actuation member of the shaft assembly; and (f) a locking feature configured to transition between a first position and a second position, wherein the locking feature is configured to prevent rotation of the end effector about the longitudinal axis when the locking feature is in the first position, wherein the locking feature is configured to permit rotation of the end effector about the longitudinal axis when the locking feature is in the second position, wherein the actuator is configured to move the locking feature between the first position and the second position.

Example 20

An apparatus comprising: (a) a body assembly comprising: (i) a housing, and (ii) a trigger pivotably coupled to the housing; (b) a shaft comprising a proximal end and a distal end, wherein the shaft extends distally from the body assembly, wherein the shaft defines a longitudinal axis; (c) an end effector secured to the distal end of the shaft; (d) a rotation knob comprising: (i) a proximal end, (ii) a distal end, and (iii) a channel configured to couple with the shaft, wherein the channel is concentric with the shaft, wherein the rotation knob is configured to rotate the end effector about the longitudinal axis; and (e) a locking feature configured to transition between a first position to a second position, wherein the locking feature is configured to prevent rotation of the end effector about the longitudinal axis when the locking feature is in the first position, wherein the locking feature is configured to permit rotation of the end effector about the longitudinal axis when the locking feature is in the second position.

V. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
    (a) a body assembly;
    (b) a shaft comprising a proximal end, and a distal end, wherein the shaft extends distally from the body assembly, wherein the shaft defines a longitudinal axis;
    (c) an end effector positioned at the distal end of the shaft;
    (d) a rotation input feature comprising a proximal end and a distal end, wherein the rotation input feature is configured to rotate relative to the body about the longitudinal axis, wherein the rotation input feature is configured to rotate one or both of the shaft assembly or the end effector about the longitudinal axis; and (e) a locking feature configured to transition between a locked state and an unlocked state, where the locking feature is biased toward the locked state,
wherein the locking feature is configured to prevent rotation of the one or both of the shaft or the end effector when the locking feature is in the locked state,
wherein the locking feature is configured to permit rotation of the one or both of the shaft or the end effector when the locking feature is in the unlocked state,
wherein the rotational input feature is configured to rotate relative to the body about the longitudinal axis to drive the locking feature between the locked state and the unlocked state.

2. The apparatus of claim 1, wherein the shaft further comprises a shaft retainer unitarily coupled near the proximal end of the shaft, wherein the body further comprises at least one boss extending distally from the body assembly.

3. The apparatus of claim 2, wherein locking feature further comprises a spring clamp resiliently biased to surround the at least one boss.

4. The apparatus of claim 3, wherein the spring clamp further comprises a set of notches extending distally from the at least one boss, wherein the shaft retainer further comprises a set of cutouts adjacent to the set of notches.

5. The apparatus of claim 4, wherein the rotation input feature further comprises a rotation channel and a key slot, wherein the rotation channel is configured to house the locking feature and the shaft retainer, wherein the key slot is configured to contact the spring clamp to transition the locking feature from the locked state to the unlocked state.

6. The apparatus of claim 5, wherein the set of cutouts are configured to contact the notches when the locking feature is in the unlocked state, thereby rotating the shaft.

7. The apparatus of claim 3, wherein the spring clamp further comprises a plurality of tabs.

8. The apparatus of claim 7, wherein the rotation input feature further comprises a key slot housing the tabs, wherein the key slot is configured to contact the tabs to transition the locking feature from the locked state to the unlocked state.

9. The apparatus of claim 2, wherein the at least one boss and the shaft retainer are coaxially aligned.

10. The apparatus of claim 1, wherein the rotation input feature comprises a rotation knob, wherein a proximal end of the rotation knob is within the body assembly, wherein the distal end of the rotation knob extends distally from body assembly.

11. The apparatus of claim 10, wherein the rotation knob further comprises an integral flange within the body assembly, wherein the integral flange is configured to maintain a longitudinal position of the rotation knob relative to the body assembly.

12. The apparatus of claim 1, wherein a proximal end of rotation input feature comprises one or more locking features.

13. The apparatus of claim 12, further comprising a trigger movably mounted to the body assembly, wherein the end effector comprises a movable member coupled with the trigger such that the trigger is movable relative to the body assembly to move the movable member of the end effector.

14. The apparatus of claim 13, wherein the trigger further comprises one or more locking features, wherein the one or more locking features of the rotation input feature are configured to cooperate with the one or more locking features of the trigger to form the locking feature, such that the one or more locking features of the trigger are configured to selectively engage the one or more locking features of the rotation input feature to thereby provide the locked state.

15. The apparatus of claim 14, wherein the trigger is configured to provide engagement between the one or more locking features of the trigger and the one or more locking features of the rotation input feature as the trigger is moved to provide movement of the movable member of the end effector.

16. The apparatus of claim 1, wherein the rotation input feature further comprises a cam slot;
wherein the shaft further comprises a set of teeth;
wherein the locking feature further comprises:
(i) a rotation lock having a set of teeth configured to engage the teeth of the shaft, wherein the rotation lock is resiliently biased to provide engagement between the teeth of the rotation lock and the teeth of the shaft, and
(ii) a first pin disposed in the cam slot of the rotation input feature, wherein first the pin is in communication with the rotation lock,
wherein the rotation input feature is rotatable to drive the first pin to thereby disengage the teeth of the rotation lock from the teeth of the shaft.

17. The apparatus of claim 16, wherein the rotation input feature further comprises a linear slot, wherein the shaft further comprises a second pin inserted with the linear slot, wherein the rotation input feature is operable to rotate the shaft via the second pin.

18. The apparatus of claim 1, wherein the locking feature further comprises a locking body rotatably fixed within the body assembly, wherein the locking body further comprises cam surfaces configured to engage the rotation input feature to place locking feature in the locked state.

19. An apparatus comprising:
(a) a body assembly;
(b) a shaft assembly, wherein the shaft assembly extends distally from the body assembly, wherein the shaft assembly defines a longitudinal axis,
wherein the shaft assembly further comprises:
(i) an external sheath, and
(ii) an internal actuation member located with the sheath;
(c) an end effector located at a distal end of the shaft assembly, wherein the end effector includes a movable member coupled with the internal actuation member of the shaft assembly;
(d) a rotation knob secured to the external sheath, wherein the rotation knob comprises a proximal end and a distal end, wherein the rotation knob is configured to rotate the end effector about the longitudinal axis;
(e) an actuator configured to move relative to the body assembly to thereby move the internal actuation member of the shaft assembly; and
(f) a locking feature configured to transition between a first position and a second position, wherein the locking feature is configured to prevent rotation of the end effector about the longitudinal axis when the locking feature is in the first position, wherein the locking feature is configured to permit rotation of the end effector about the longitudinal axis when the locking feature is in the second position, wherein the actuator is configured to move the locking feature between the first position and the second position.

20. An apparatus comprising:
(a) a body assembly comprising:
(i) a housing,
(ii) a trigger pivotably coupled to the housing, and (iii) at least one boss extending distally from the housing;

(b) a shaft comprising a proximal end, a distal end, and a shaft retainer defining a set of cutouts, wherein the shaft extends distally from the body assembly, wherein the shaft defines a longitudinal axis;

(c) an end effector secured to the distal end of the shaft;

(d) a rotation knob comprising:
   (i) a proximal end,
   (ii) a distal end,
   (iii) a channel configured to couple with the shaft, wherein the channel is concentric with the shaft, and
   (iv) a key slot,
   wherein the rotation knob is configured to rotate the end effector about the longitudinal axis; and (e) a locking feature comprising a spring clamp resiliently biased to surround the at least one boss, wherein the spring clamp further comprises a set of notches extending distally from the at least one boss and adjacent to the set of cutouts of the shaft retainer, wherein the locking feature is configured to transition between a first position to a second position, wherein the locking feature is configured to prevent rotation of the end effector about the longitudinal axis when the locking feature is in the first position, wherein the locking feature is configured to permit rotation of the end effector about the longitudinal axis when the locking feature is in the second position, wherein the channel of the rotation knob is configured to house the locking feature and the shaft retainer, wherein the key slot is configured to contact the spring clamp to transition the locking feature from the first position to the second position.

* * * * *